US011473092B2

(12) United States Patent
Yoshida

(10) Patent No.: US 11,473,092 B2
(45) Date of Patent: Oct. 18, 2022

(54) TRANSFORMATION METHOD OF GRAM-POSITIVE BACTERIA

(71) Applicant: NATIONAL UNIVERSITY CORPORATION KOBE UNIVERSITY, Kobe (JP)

(72) Inventor: Kenichi Yoshida, Kobe (JP)

(73) Assignee: NATIONAL UNIVERSITY CORPORATION KOBE UNIVERSITY, Kobe (JP)

( * ) Notice: Subject to any disclaimer, the term of this patent is extended or adjusted under 35 U.S.C. 154(b) by 58 days.

(21) Appl. No.: 16/770,519

(22) PCT Filed: Dec. 7, 2018

(86) PCT No.: PCT/JP2018/045055
§ 371 (c)(1),
(2) Date: Jun. 25, 2020

(87) PCT Pub. No.: WO2019/112032
PCT Pub. Date: Jun. 13, 2019

(65) Prior Publication Data
US 2021/0180073 A1    Jun. 17, 2021

(30) Foreign Application Priority Data
Dec. 7, 2017    (JP) .............................. JP2017-235374

(51) Int. Cl.
    *C12N 15/75*    (2006.01)
(52) U.S. Cl.
    CPC ................................... *C12N 15/75* (2013.01)
(58) Field of Classification Search
    None
    See application file for complete search history.

(56) References Cited

U.S. PATENT DOCUMENTS 6,991,786 B1    1/2006    Filutowicz

FOREIGN PATENT DOCUMENTS

| EP | 1 313 864 A2 | 5/2003 |
| JP | 2004-507470 A | 3/2004 |
| WO | WO 02/18605 A2 | 3/2002 |

OTHER PUBLICATIONS

Berglund, "Environmental dissemination of antibiotic resistance genes and correlation to anthropogenic contamination with antibiotics", Infection Ecology & Epidemiology, vol. 5, 2015, pp. 1-10.
Davies et al., "Origins and Evolution of Antibiotic Resistance", Microbiology and Molecular Biology Reviews, vol. 74, No. 3, Sep. 2010, pp. 417-433.
Dordet-Frisoni et al., "Chromosomal Transfers in Mycoplasmas: When Minimal Genomes Go Mobile", MBio, vol. 5, No. 6, 2014, pp. 1-11.
Hoch, et al., "Transformation and Transduction in Recombination-defective Mutants of Bacillus subtilis", Journal of Bacteriology, vol. 93, No. 6, Jun. 1967, pp. 1925-1937.
Ichinose, "Identification of OriT sequence of conjugational transfer plasmid pLS20", Report of research results of FY 2013 Mori Foundation, 2013, URL:https://www.kri.sfc.keio.ac.jp, pp. 1-6, with partial English translation, 11 pages total.
Itaya et al., "Conjugational transfer Kinetics of pLS20 between Bacillus subtilis in Liquid Medium", Biosci. Biotechnol. Biochem., vol. 70, No. 3, 2006, pp. 740-742.
Miyano et al., "Rapid conjugative mobilization of a 100 kb segment of Bacillus subtilis chromosomal DNA is mediated by a helper plasmid with no ability for self-transfer", Microbial Cell Factories, vol. 17, No. 13, Jan. 27, 2018, pp. 1-10.
Ramsay et al., "Diverse mobilization strategies facilitate transfer of non-conjugative mobile genetic elements", Current Opinion in Microbiology, vol. 38, 2017, pp. 1-9.
Staddon et al., "Genetic characterization of the conjugative DNA processing system of enterococcal plasmid pCF10", Plasmid, vol. 56, No. 2, 2006, pp. 102-111 (15 pages total).
Strand et al., "A New and Improved Host-Independent Plasmid System for RK2-Based Conjugal Transfer", Plos One, vol. 9, No. 3, 2014, pp. 1-6.
Suwanto et al., "Chromosome Transfer in Rhodobacter sphaeroides: Hfr Formation and Genetic Evidence for Two Unique Circular Chromosomes", Journal of Bacteriology, vol. 174, No. 4, 1992, pp. 1135-1145.
Tanaka et al., "Isolation and Characterization of Four Plasmids from Bacillus subtilis", Journal of Bacteriology, vol. 129, No. 3, Mar. 1977, pp. 1487-1494.

(Continued)

*Primary Examiner* — Suzanne M Noakes
(74) *Attorney, Agent, or Firm* — Birch, Stewart, Kolasch & Birch, LLP

(57) ABSTRACT

One objective of the present invention is to provide a novel simple and efficient transformation method for gram-positive bacteria, the transformation method being capable of introducing a large-sized DNA into a host DNA of the gram-positive bacteria without damage. In addition, another objective of the present invention is to provide a method in which desired DNA segments are accumulated in a chromosome of a recipient (recipient bacteria) to enable an artificially designed huge DNA to be constructed, and in which a transformed cell does not cause any problems in terms of controlling the natural environment. The present invention relates to a transformation method for gram-positive bacteria by conjugative transfer, characterized to use a helper plasmid having an origin of DNA transfer (oriT) region is inactivated. Preferably, the helper plasmid is a plasmid in which an oriT region is inactivated from pLS20cat. Furthermore, this transformation method is preferably a method in which donor bacteria have a helper plasmid having an origin of DNA transfer (oriT) region is inactivated and a chromosome DNA or plasmid incorporating an origin of DNA transfer (oriT) region, and transfer the same to the recipient bacteria.

9 Claims, 6 Drawing Sheets

Specification includes a Sequence Listing.

(56) References Cited

OTHER PUBLICATIONS

Extended European Search Report for European Patent Application No. 18886941.6, dated Oct. 27, 2021.
Miyano et al., "A novel method for transforming the thermophilic bacterium Geobacillus kaustopbilus", Microbial Cell Factories, Vo. 17, No. 127, 2018, pp. 1-13.
Office Action dated Sep. 27, 2021 for Japanese Patent Application No. 2019-558291, with English Translation.

SEQUENCE LISTING

```
<160> NUMBER OF SEQ ID NOS: 35

<210> SEQ ID NO 1
<211> LENGTH: 37
<212> TYPE: DNA
<213> ORGANISM: Artificial Sequence
<220> FEATURE:
<223> OTHER INFORMATION: Primer etc.

<400> SEQUENCE: 1
gagtcagaaa acagacgcat aaacgctaac ggtcagc                              37

<210> SEQ ID NO 2
<211> LENGTH: 46
<212> TYPE: DNA
<213> ORGANISM: Artificial Sequence
<220> FEATURE:
<223> OTHER INFORMATION: Primer etc.

<400> SEQUENCE: 2
ctaataccgt tccccgagaa gcttcactaa attaaagtaa taaagc                    46

<210> SEQ ID NO 3
<211> LENGTH: 19
<212> TYPE: DNA
<213> ORGANISM: Artificial Sequence
```

```
<220> FEATURE:
<223> OTHER INFORMATION: Primer etc.

<400> SEQUENCE: 3
agagcgtaag aaacgcatc                                               19

<210> SEQ ID NO 4
<211> LENGTH: 19
<212> TYPE: DNA
<213> ORGANISM: Artificial Sequence
<220> FEATURE:
<223> OTHER INFORMATION: Primer etc.

<400> SEQUENCE: 4
tgcgtctgtt ttctgactc                                               19

<210> SEQ ID NO 5
<211> LENGTH: 18
<212> TYPE: DNA
<213> ORGANISM: Artificial Sequence
<220> FEATURE:
<223> OTHER INFORMATION: Primer

<400> SEQUENCE: 5
ctcggggaac ggtattag                                                18

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
cgaagatctg cctactgaac                                              20

<210> SEQ ID NO 7
<211> LENGTH: 25
<212> TYPE: DNA
<213> ORGANISM: Artificial Sequence
<220> FEATURE:
<223> OTHER INFORMATION: Primer

<400> SEQUENCE: 7
taaataacat gactgtggaa atgac                                        25

<210> SEQ ID NO 8
<211> LENGTH: 44
<212> TYPE: DNA
<213> ORGANISM: Artificial Sequence
<220> FEATURE:
<223> OTHER INFORMATION: Primer

<400> SEQUENCE: 8
gcttgagtca attccgctgt cgttagtctt cgatgacgag attg                   44

<210> SEQ ID NO 9
<211> LENGTH: 77
<212> TYPE: DNA
<213> ORGANISM: Artificial Sequence
<220> FEATURE:
<223> OTHER INFORMATION: Primer

<400> SEQUENCE: 9
ctgattgggt aggatccccg agaaagagca atctcgtcat cgaagactaa aaaagaaac   60
```
acttatttga acagatc                                                          77

<210> SEQ ID NO 10
<211> LENGTH: 19
<212> TYPE: DNA
<213> ORGANISM: Artificial Sequence
<220> FEATURE:
<223> OTHER INFORMATION: Primer

<400> SEQUENCE: 10
gcgtcttctt aaaacgctg                                                        19

<210> SEQ ID NO 11
<211> LENGTH: 22
<212> TYPE: DNA
<213> ORGANISM: Artificial Sequence
<220> FEATURE:
<223> OTHER INFORMATION: Primer

<400> SEQUENCE: 11
cgacagcgga attgactcaa gc                                                    22

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
cggggatcct acccaatcag                                                       20

<210> SEQ ID NO 13
<211> LENGTH: 33
<212> TYPE: DNA
<213> ORGANISM: Artificial Sequence
<220> FEATURE:
<223> OTHER INFORMATION: Primer

<400> SEQUENCE: 13
aaagagcaat ctcgtcatcg aagactaaat ttc                                        33

<210> SEQ ID NO 14
<211> LENGTH: 29
<212> TYPE: DNA
<213> ORGANISM: Artificial Sequence
<220> FEATURE:
<223> OTHER INFORMATION: Primer

<400> SEQUENCE: 14
ttgttaacgc tccttttcat cgatttctg                                             29

<210> SEQ ID NO 15
<211> LENGTH: 52
<212> TYPE: DNA
<213> ORGANISM: Artificial Sequence
<220> FEATURE:
<223> OTHER INFORMATION: Primer

<400> SEQUENCE: 15
cagaaatcga tgaaaaggag cgttaacaag agtgtgttga tagtgcagta tc                   52

<210> SEQ ID NO 16
<211> LENGTH: 56
<212> TYPE: DNA
<213> ORGANISM: Artificial Sequence

```
<220> FEATURE:
<223> OTHER INFORMATION: Primer

<400> SEQUENCE: 16
gaaatttagt cttcgatgac gagattgctc tttgagtgtg ttgatagtgc agtatc        56

<210> SEQ ID NO 17
<211> LENGTH: 26
<212> TYPE: DNA
<213> ORGANISM: Artificial Sequence
<220> FEATURE:
<223> OTHER INFORMATION: Primer

<400> SEQUENCE: 17
ctacattccc tttagtaacg tgtaac                                          26

<210> SEQ ID NO 18
<211> LENGTH: 22
<212> TYPE: DNA
<213> ORGANISM: Artificial Sequence
<220> FEATURE:
<223> OTHER INFORMATION: Primer

<400> SEQUENCE: 18
gatcgtgaaa ggccccaatg tg                                              22

<210> SEQ ID NO 19
<211> LENGTH: 61
<212> TYPE: DNA
<213> ORGANISM: Artificial Sequence
<220> FEATURE:
<223> OTHER INFORMATION: Primer

<400> SEQUENCE: 19
gaaatttagt cttcgatgac gagattgctc tttgaagcaa aggattgaaa atgaaaaagc     60
g                                                                     61

<210> SEQ ID NO 20
<211> LENGTH: 57
<212> TYPE: DNA
<213> ORGANISM: Artificial Sequence
<220> FEATURE:
<223> OTHER INFORMATION: Primer

<400> SEQUENCE: 20
cagaaatcga tgaaaaggag cgttaacaag aagcaaagga ttgaaaatga aaaagcg        57

<210> SEQ ID NO 21
<211> LENGTH: 57
<212> TYPE: DNA
<213> ORGANISM: Artificial Sequence
<220> FEATURE:
<223> OTHER INFORMATION: Primer

<400> SEQUENCE: 21
gttacacgtt actaaaggga atgtagcact attttttca tttgcatcac tccaaac         57

<210> SEQ ID NO 22
<211> LENGTH: 26
<212> TYPE: DNA
<213> ORGANISM: Artificial Sequence
<220> FEATURE:
<223> OTHER INFORMATION: Primer

<400> SEQUENCE: 22
```

```
atcagcgaaa gcacaaacac aaaacc                                          26

<210> SEQ ID NO 23
<211> LENGTH: 28
<212> TYPE: DNA
<213> ORGANISM: Artificial Sequence
<220> FEATURE:
<223> OTHER INFORMATION: Primer

<400> SEQUENCE: 23
atgataaaat gaccaccgaa gaattccg                                        28

<210> SEQ ID NO 24
<211> LENGTH: 58
<212> TYPE: DNA
<213> ORGANISM: Artificial Sequence
<220> FEATURE:
<223> OTHER INFORMATION: Primer

<400> SEQUENCE: 24
gaaatttagt cttcgatgac gagattgctc tttcactttc atgtgaatcc ctcctgcc       58

<210> SEQ ID NO 25
<211> LENGTH: 55
<212> TYPE: DNA
<213> ORGANISM: Artificial Sequence
<220> FEATURE:
<223> OTHER INFORMATION: Primer

<400> SEQUENCE: 25
gttacacgtt actaaaggga atgtaggaaa ctatgacagt actgacactc agggc          55

<210> SEQ ID NO 26
<211> LENGTH: 22
<212> TYPE: DNA
<213> ORGANISM: Artificial Sequence
<220> FEATURE:
<223> OTHER INFORMATION: Primer

<400> SEQUENCE: 26
gacgagctca acctttggca gc                                              22

<210> SEQ ID NO 27
<211> LENGTH: 23
<212> TYPE: DNA
<213> ORGANISM: Artificial Sequence
<220> FEATURE:
<223> OTHER INFORMATION: Primer

<400> SEQUENCE: 27
gccaaatgga ggccgtatgt cag                                             23

<210> SEQ ID NO 28
<211> LENGTH: 64
<212> TYPE: DNA
<213> ORGANISM: Artificial Sequence
<220> FEATURE:
<223> OTHER INFORMATION: Primer

<400> SEQUENCE: 28
gaaatttagt cttcgatgac gagattgctc ttttgaccat ttttcagcct ccttttctt      60 tttc                                                                  64

<210> SEQ ID NO 29
<211> LENGTH: 61
```

```
<212> TYPE: DNA
<213> ORGANISM: Artificial Sequence
<220> FEATURE:
<223> OTHER INFORMATION: Primer

<400> SEQUENCE: 29
gttacacgtt actaaaggga atgtaggatt gtaaaagcaa aagggtgtt tcaataaaag       60 g                                                                     61

<210> SEQ ID NO 30
<211> LENGTH: 31
<212> TYPE: DNA
<213> ORGANISM: Artificial Sequence
<220> FEATURE:
<223> OTHER INFORMATION: Primer

<400> SEQUENCE: 30
ggcttgggat cgatacaagt tctttaatga g                                    31

<210> SEQ ID NO 31
<211> LENGTH: 26
<212> TYPE: DNA
<213> ORGANISM: Artificial Sequence
<220> FEATURE:
<223> OTHER INFORMATION: Primer

<400> SEQUENCE: 31
ttcggggacg aaaatagca cagatc                                           26

<210> SEQ ID NO 32
<211> LENGTH: 58
<212> TYPE: DNA
<213> ORGANISM: Artificial Sequence
<220> FEATURE:
<223> OTHER INFORMATION: Primer

<400> SEQUENCE: 32
gaaatttagt cttcgatgac gagattgctc tttctgctga tatgaaaaac ctttgccg       58

<210> SEQ ID NO 33
<211> LENGTH: 50
<212> TYPE: DNA
<213> ORGANISM: Artificial Sequence
<220> FEATURE:
<223> OTHER INFORMATION: Primer

<400> SEQUENCE: 33
gttacacgtt actaaaggga atgtagagcc ctctgccttt ttggttcatg                50

<210> SEQ ID NO 34
<211> LENGTH: 35
<212> TYPE: DNA
<213> ORGANISM: Artificial Sequence
<220> FEATURE:
<223> OTHER INFORMATION: Primer

<400> SEQUENCE: 34
gctttgttag tcttcttttg aaagtcagaa aaagc                                35

<210> SEQ ID NO 35
<211> LENGTH: 65512
<212> TYPE: DNA
<213> ORGANISM: Bacillus subtilis

<400> SEQUENCE: 35
```

-continued

```
tgtgttttaa aatgtttgat gatgccgata agtattagga ctagttttgt ttttgaatag    60
ctggagggaa gtgtatgttg tccaaagtaa aaaaagtacc gtctccctat gtaggcaatc   120
tgttgaataa atggcatgac tatattatgc aggagaaggt tcatgagtct atagagaaaa   180
gaactgaaat aaagcaattg ttaagtcagg ctgaagataa taaggacctg gttgattatt   240
ttattctact ggatcatcgt catagccttt gttttgatca agaggcatct atgggtgatg   300
tcgttaatat gttaagtaag ggaagtcatg atcttttaat aaattttat tttgaattgt    360 ttgcagggga ttatgagttt tttaaaaaaa attatgttaa agcaatttct ttttatgaaa   420
aagctgaaca aaagttatcg agtattccca atattgagga aacgaagttt gcggagtttc   480
actataagat tggagttgct tattatgaga ttgaccagca tttggtgtca gtcaacaaag   540
taactaaagc cagggatatt tataaaaaaa gtgatatgtg gaacctcgaa gctattcagt   600
gcagtttggt ggtcggtatt aatttgtatg atatggggcg tttagatgat gcggatgcat   660
attttcgtga tgccttgact gaggccttgg atcatggcta tgataagcct ataactaaga   720
tttaccacaa tcttggatta gtccattggc aaaaaggttc tcttgaatta gctctgcatt   780
attttaggga agcttattcg catgaatggt tgagggattc gcctaaagga cagcaaactg   840
tatacatgct ttcaagagta ctgtatacaa tggggcaaaa tgaagaagct tatcactggt   900
atgaattagg gatagaaatg gcgcgtaaat ttgatgatca tgagtataaa gcaaaacacg   960
acattcttta tcatctttat gagcagcctt caatcgatga agtaaagcaa tctttagctt  1020
tcttagaaga gcgtaatctt tggccggacg tatccaaaat tgcaaaaggt atttcagagc  1080
tttatgaaaa aaaaggtgat ttagtgacta gtcacgaatt tttgaaaaga gcttttatg   1140 ctaaagagca aattcaaaga ataacggagg cgttaggatg aagaaaatta atggttggat  1200
tgtcgttgct ttgcttgctg ttactactgt aggagctgca gcagctatac aatacactaa  1260
taatgctgat tctcctggac aatttcaagt agcccaaaaa gggatgtatt aaaagctgac  1320
caataagtgt cagcttttt tgtgttcgat cacggctgca gctgaggaga agatccggcc  1380
tgaatccgga acccaggaag ccaggcgcct atgttcgaca gctgaagaaa gagatcgata  1440
agctattgat cggtaatcag taaaaaaagg actgcactta ggctagtcct tttttaattt  1500
catgtattca tttctaattt ttaataattc tatctcttct ttaacgcgct ctatatcctt  1560
ttctgaaagc ccagtaacat caaaaaaacg aataacacta ttattttcac ttgattttaa  1620
ctggtcaatt tgattttgaa tttgattgat acttgcctca gttaatccag ttaaatcaaa  1680
taattttatc tgttttgaag tatctttatc tttctcttta acatgatctt cttccattga  1740
tgctatatac tccattattt gaagcatttc tatattagga atggagagcg ccgttgccaa  1800 cttttttaata actgcctgtg tcggtctttt tctttcacct ttttcaagca tggaaatata  1860
agcagatgat aaccctgtat catttgctac ttgtgtttgg cttaaccctt tttgttttct  1920
tttttctaac aagtatttag agagatcaaa ttgctctcta ttgcccactt ataccacctc  1980
gcaaaataaa ccctgtatac ggtctagcgc ttacaatttt tcgcgttttt tttactcagt  2040
gaaaaaaacc ggttaaaaat ttcactgaaa tactttacag ttaaaaaaat gtctgttatc  2100
ttagtgaaag agtcagtgaa aaaaatgcag aataaggttt tttgttgtta atctcaaaca  2160
atttctgtgt aaaaagaact agaattcaac ttttgtttta accaacgtat tcactgttgt  2220
ctctgaagtt ttaactacca gttaatttaa ccgtatgtat gtgtattaat catacactat  2280
caaagtgtgc tatcacaatg tagtcagtta ataataagtt tagtaaaaac aggataaggg  2340
ccatcaaaat catgctgcaa cttggttttg atatagctca cagtgaaagt tagtgtgaac  2400
```

```
ttgccccatt tattgtattc atacatcatt ttagctttaa aagagaggca tcttttgaag   2460
taaaattcat ttggatgtat gtttatcaat ttggagctgt cagactaact gacagctttt   2520
tttgttgtct ttacactgat tgaaaattta gggagggaat agcttggcta aagttaaatt   2580
gctcgaaaaa aaaatgactg aaaaagatgt tttagagtat ggaagctctt taagattgtt   2640
tgacggcagc actcatgtgt tgatcggtaa ggattgttta catactcata caaaaaataa   2700
aagaccgatt tcacaatgtt attcggatat tcgaaacgtg aagaacgttg agggtgttat   2760
tgtgggaaaa cgggtttctc cgcattctag tcttcttttt acgactgaag cctttcagcc   2820
ggcaagaaaa gtaacccagg tatataaagc tccaaaaatg ccgcgtagaa gtacacaagt   2880
acggccgaga atacctctg aagagctaa gaaggtatca gttcttttaa gtgaaactgg   2940
atatgcaaat gttcatcagc tgaaacaagt gttacttgat gctggtgcta aaaaagtcca   3000
aacatataac acaagcagag gcattgctat cgtttgtcat cctaatccta actatttgct   3060
acaaaaagta atttctgaat aaagtgaggt tgatcaggat tcacacgtttt atcagtgatt   3120 aagctgataa agaattaaat attagggaag gtcccctcc aaaggtataa cggccatgca   3180
atacctttgg gtgaacattt cttcttggcg cgagtgacgg ttttcaccgg tcgtagacgg   3240
caagtttggc cttacattat cagattcaga tgaagttaag tctgaatact tggctgatat   3300
agagttccgt gagtaacaac tgctacaaac tcacgatttt ggactgtttc attgataaac   3360
gtgtgaatcc tggcttccaa gtcaaattac atcatatgtt tttaactcaa accatagtaa   3420
aattgtgaat ggaaaaatat atttaaaaag gtgttgagtg taagtatgag aaagaaattg   3480
gctgctggta ttgttgccgg tgcaattatt ttaggagtgc ctggctatac aatttttcat   3540
tcataccaag caaatgctga agaagctcgt gtgttagaca atgcaacgga tgcagttaac   3600
tcattatatg cttctaaaaa atataattac ttggctgatg gggtttcaaa gaatgatatt   3660
caaaaggctc agaagttagt atccgatgta gctgattcta agaaacagaa atcattagca   3720
gaaaaagcat ctaatgctgc gatcatgtta gaggcctcaa atgcagttaa agaggatatc   3780
gttgacgggg tgatcgttga tgatctcaca aagtctattc tttctgttac caaggaaagc   3840
gtagataagg taaagccgat cagcaaagat ttgtataaag atttatctaa agacttatct   3900
aaagcttatg atcaaattga acaaatagac aaaacaaaaa aattactcaa agatgcgaag   3960
aaagattgga attcctataa aaagattgaa aagaagtaa ataagatttc caatcagact   4020 gcgaaaaga gtctgaaaaa acagcttgaa acgctaaaaa agagaattga agatcaagag   4080
tctataagca aaaaagcgaa agaaaagctg aatgagattg agaaaacgtc acagaaggac   4140
agtgacagta aagcagcaaa cgacagcagt caagtaagca caaacgataa tgaaaatgct   4200
acttcaagtc cggcatcaag taatacttct gcaacacaga ataaatcagg tagctcgtcc   4260
aattcaagca gcagttcggg atcatcgaat tccgggtaca gctcatattc aaacgggtct   4320
agtaaatcaa gctccaacac gaaatcatac tcaaattctt cttcatcaag atcctataca   4380
tctaagtcaa attcgggcag cactagccat agcgaaagta aaaaaagcag aactggaagc   4440
agttcagctg ggagcagcaa taatcatca agcagtaagt cgtcttccag cacatctaaa   4500
agtaaacaat cccaaaacaa caccatgaaa atgcgaacg attttgttaa tgactttaac   4560
agtggaaatt ataatcatgt tggtagtggt aataatggga caggtaataa ctacgatgtg   4620
tatgagagag gacagtaagc attgggtgat aacacgaata aatacgtggt ctctctgatt   4680
tcggtattca ttgctggttt aatagtgtta attggtctta tggcgttaag tggggtgtat   4740
```

```
gcacagattg aggaaaggca gtctgaaaaa agatatcagg cagtttcaac tcaattaggc    4800
attccaaaag ctgagatcct aataacacct tctgcccatg acggaatcta tactgtaaaa    4860
gctaacaaca ggttatactt agtagagttt gacacctcag ataaaaaaat tgcacatatg    4920
actgaagaac ggactaattg attagtccgt tctttacgtt ttttaataaa gaaaaagggg    4980
cttgtggaat gaaaaagatt ttgctaattc taacatttgt aatcctggca ttttcagctt    5040
taaccggctg tagcagtgag agctgggatc gcacagtaaa agatcatgaa tcaagtgtta    5100
acgggctgaa acgcacagca acggtatatg accaaaatgg gaaggtcatc aagacgtata    5160
aaggcaagtt tgatgtagag gtcaatgatt acggaaataa agttaagttt gacattgatg    5220
gtaagcgcgt ggttatcaat aacgcgatag tgattgtaga agaggataaa tgatcgaata    5280
gcaaggggga ggtgatgatg aatgttccta ttttgaggtg aaaggagata gccatggatg    5340
aaaaagctat tttaagtgat gaagtggcca aggataggat attaaaccga atttccagtg    5400
aagggattag aataagatct tccttttcta agtctgcgac tggcaatat acgtattatt     5460 tgggagaaga taagataccg ccgacaattg aagtaccaca attcactgat ctcagtgaat    5520
taatacaggc atttgcgttg gcgcatgaat tgggacatca ttacgtatac caaaggattt    5580
caagaaaaaa agctcggctt ttcaaatctg gaatgacttg tacaacgtat tggaatgaga    5640
aattggcatg gcgggaagcc gaaaaaatac tgaaggagga agggattcta gttgacgagc    5700
agaccaactg ctcttttcttt aagtacaaga cattttgctt aaacacttat aaagatcagg    5760
tggtacattc tattagcagc ccgttcaagt tcttgttcgg cagtgttctg cttctaatgt    5820
agctatacat cggactttat attctacttg gtattgggct ggtttttttcc gcgaattcta    5880 tcccaatacc atttgatgaa tttttagggt tcagttcttt aaataaaaat gaactcctta    5940
ctgtcgttcc taaacttgtt tacatcttgt taagtttagc cactatgtat aagttttgtt    6000
ggtgttactt tttaaagcgc tcatttagac cggctctatt ttattttgta acattgtttc    6060
tctcacaatt ggcccctatg gtgctctaga gagaaaaatg gatttggaaa atgaggtgga    6120
aaaatggatt tgaataaagg tattgaagaa ctgcaatctg aaaatagtct caaggggta     6180 ctattagagg gacgcctaga attcaaaaag tttcttaaaa aaaataacca tttagatatt    6240
aaggatatcc actggcaagc aatacaacat aattcgtgga tagaacacta ttttttttgtt   6300 aagtacaccg agaagaatgg tgaattaaag gtataggagg aatctttgtt gaggcaaatc    6360
attatacttc ccccatcggg atttgtttct ttgagtttgt ttaagctttt gccatacagc    6420
acaataagaa aggggtgatc gaagtgattc acatagtgta taaagaatc ttgataatgc     6480 tatcaagtgt tgtagcaatt gccgcagcgc tttttttagt gccattttttc acctcatcgg    6540 ccgaagctgc tacagctgtt gccacaggtc cgtattcatg gaaagatccg cacggcatta    6600
ctcatgaatc agcttacatc aaaataggag acaccattgt ttactgtatt gatccagata    6660
agcctgcacc ttatggcggt cattcgtata aaaccccgaa gcgtcaatat gatgatggcg    6720
tcaaagccat tctttattac gggttcggcg gtgacggtaa tgaaattgga aagacaatga    6780
cggatatggt caaaacctat gtcgctctta caactggct agatggaaaa agggatcaaa     6840
gaacatatag taaccaggat gccgaagtgt ggaagttaat tcaacatgct aaaaaaggtg    6900
atgctccgag ctaccaggta tccttcagca aaactaaagt aggcagctct gtttccggtg    6960
atcagcaaaa atcagaaacc attaagctga acgggaaagg aacagctacg ttaaccgttc    7020
cttcaaaggt aacgatacac gtgatcggcg gcaaaaccca aaagggcggc catatcacta    7080
ttcatgatgg ccaatcattt tatttcactg cacctttaga ttatggatct gactacgaca    7140
```

```
cagggaatgt taatggtgag atcagacagc tggcgtccct gctttatcta cctaatacga    7200
gcagctatca acggctgatg tcaagtacat ttgtggttga tccggttgtg cagctggtt     7260 ttaccgttca ttttgaaaag cgtcaaaaac aaattacggt ggttcataag gacaagtacg    7320
aaggcacggt cttaaagaaa gtaaagagt  ctaaaaatat cggaaccaat tacagctatt    7380
cacctgagaa gaaaatcgta aaagatggga aaacctatgt gcccgttaaa acagaaaaga   7440
aaaccggtaa attgggaaac aaagatatca ctattacttt tgagtatgca ttgcaaagga    7500
aaataactgt gctgcacaaa gataaccggg accacacgtt gatcaagaaa caagtatata    7560
ccaaaaaacg aggcgatacg tattcgtatg gtccattaac caatttgaaa agaacaatt     7620 acacatatcg tcctgtctcg gataaaaagg taactggtac cgttggaaaa gatgatgtaa    7680
caattactat ttattatgat gttccattga tcaagaccag ccttgataag cttcaaatat    7740
atacggctcc ggctgctgat ggtctgccgg ttaaggttta tctttctaag accaacattt    7800
ataaaaatga caccaagggc atgaccacag caaaaataaa tgtcagcttg tatgacggga    7860
aacagctgct aagcaaaaaa acatatacag cacagagttt gccgaagaat gtaaatttca    7920
ctgtgccggc aaagaattta aaggttaacg caaataaact ctatacggtc aaattagagg    7980
gttttaatga aaatgatgta gatgtacctg acaaggcaaa agaactctct acgaagggtt    8040
atacgagttc tgaagacaaa gtttctgtgt ctatgaaagt tgtagttaaa aatcagggat    8100
ctgttaaacg cgtagttatg acagaagtaa ccccaacaac tgctatgaaa agctattttg    8160
aaacaatgac atatcaaggg cagctgcttc ctaaacggaa aaccggttat ggcagcgagc    8220
aaaatcttgc tttcatatat gagaacatgc ttcaaaaaga cgatgatgat atcaaattcg    8280
attttaaagt acctgaagag ttgatggata cttacttaaa ctattctgtt aaagacggta    8340
aagctatatt ccctatggat gttgcagcat ctaagaaatc aagcaccgca gacaatttaa    8400
tccgggaaat gtcatttgtt ttccctcacg taaatgtgga aaaagaaact ggcagcttat    8460
tcacagatca gcaagttaaa gcaaaagaca aacgcttgaa aaacgctgtt cgtgacggag    8520
ggaacaaatt ttacactcct atttgggcgg aattaggcag ctatgatgtt tcttatactt    8580
caagcaaagt aggggttaac aaagtgacta ttgaattgaa ggataagctc acactatttg    8640
cttatatgta cggccatatg aattcagaaa caaggatca  ggacgaaata atgctaacgc    8700
cgattaatgc tgatgatcct ttccctaacg gtacacctga cggctggtca caaagtgata    8760
ttaattggtt gaagaaataa ccttttcaac tgtttggagg aaaaagtatg gagaaaagct    8820
gtttcacttt taccaccaag aatagggttg aggccatcac aaaaataacg agactcatat    8880
ctgaaggcaa attaatcagc gttaattcta gaagaattaa agaatccaca aaaaggcaga    8940
gccttcagcc gatagacgat ttatatacag gcactattga gtacacgatt gtcagctaca    9000
aagaatagca gcagagcaat cagaaaggga aggtaatggg ttatcaagat aaaggaatag    9060
acgtacgttt ctaatatttt ctactcaatg taggttatat tgtacttggt atagacagtg    9120
tgcaatatta ctctaaagcg agtttgatta tgttctgtgt tctcgtagcc tgtaatttaa    9180
gcatgctgtt tttttatggt gtataccta  gagaacaaag acgggatgat ctttgtattg    9240 tgaaaaaga gctaagtaga catttaaaaa agatgtagat gaaattgaa tttgagaacc     9300 atcacaaaat tggacataga ttgtatggta tagaagcaga cggcgtttta tatcgcgttt    9360
tagtaaagga aaaagccgag atagttaaag ggaactaact tttagttccc tttttttgat    9420
acctggagaa aatcgaggtg agaaaatgaa aggttcgatt accactttag gacttgtata    9480
```

```
tattggcctg tttctgctga tggtcatcat ttcttatcac accgaggcat accgacacaa    9540
ttcgattata agcactatga ccgaatcagg acagatagca agtatcaaca gcattgataa    9600
aagttcccgt gtggaagatg gacgtgtaga ggttacagaa gagagcttca aaaagaaatt    9660
caaaactctc tttgaacaaa acagcaatat taaactatca ggaactaaat ataactttga    9720
ttttttaaag acagcagacg gcggaattaa ggctgtccgc gttaaaatca cagacgaccg    9780
caactcaaaa tatcaagtaa cgttcgtgtc gaattttgtc agttgaggag gaaataaaat    9840
gattagtcca gatacaatta aaggtatata tacagatatc cgagagaaaa acccagaaat    9900
tgtgttagaa gctttcactt caaaagaagc aagggaagtt atgtggaaac tggttgctga    9960
agataatgct actgttttgg atactgataa aaaagtagat tatgtaatgc aggaaatggt    10020
tggcctgggt gtcattgaaa cgattataaa acaacatgat acggttacag atattacttt    10080
taatgcaaat caattgattg ttagaagaag cgatctcaaa gacccttatc catacgaaga    10140
tcaggaaata actgaggagt atattttaaa gatcatccaa aagttcgcta atgcagtaga    10200
aaaagaattt acacctaaag atcctatctt ggatgcctct ttggggaatt tgcgaatcaa    10260
cgctgttcat aaagctgtat cgccatatgg gaccacaatg gcaattcgcg tatcacgtcc    10320
aaagctggca cttaccaagg agaattttc agactttgct cctgactata tgtatgaatt    10380
ttttaaggct gctgttgcag caaaagctaa cattggtatt tctggtgaaa caggttccgg    10440
taaaaccgaa tttcaaaagt ttttgttaag ctttatacca tttggagaaa aaatcatttg    10500
gattgaagat acgcgggaag acaccttaa agagttgttt ggggacacaa aagatattca    10560
tagctggctt acttctcctg gggtaactat tacagatttg gtaaaggcgg cactcagaaa    10620
caaccctaaa tggatctgcg tatctgagac gagaggtatg gaagcatatg aaatgctgca    10680
agctgttttg tccagtcaca gtatcataac cactttgcat gcaaatgatg ttaagactat    10740
tcctcgaaga tttatcaata tgatgaaaat gggctaccaa ttagatgaaa aatcaacact    10800
tggtgatatt tatgaaaact tccatttagg agttcatttg aaagccacag agttgaatgg    10860
caaaacggtt agatatctga gtgaggtttc cgagtacaat gctgatggat ctgtaaaaat    10920
gatcttcaag caggagcaca tagacgggcg attcgtgcaa acagtaggta aaataagtca    10980
gaaattaaag gaccgcatgt tagaacacca cgtcaaatat agtggtttac ctgttagggg    11040
ggaatagtgt gaagaaaaag gtatattcgc tagatgagct taacgcttat aaagtcgcgt    11100
atggaaagcc tattgaacga aaagagcttt taatgtcttt gataaaacca tttgctgtgg    11160
ttttttgtttt ttcttatgca ctgttttatt actggtggct cagcttaata ttaggtgtgt    11220
ttgcaatgtt ttatggctat cgtgttatga tgccgcagtc aattaagcgt gtatacgagg    11280
ctaatgcttt tcaagagcgt cataactttg ttaacaactt aactcaaatc cttaccaatt    11340
ccgataagac tatgttaaaa gcattagaaa cagtctcgga tcgtgcaaaa ggagaattta    11400
aagaggatct tcttcagctg cgaggagcgc ttcaaggtgc ttctactgaa gagattcatg    11460
cagcatttaa agagtttggt gagaaatata agcatgacgc aatatttgac ttgtatatcg    11520
aacaattaac tactgctact attgagggcc gtacaaatat tgaaacgatt aaagatataa    11580
aatcactaca caatgaattg aaacaagaac aagataaatt tttacagaaa aagaaacgag    11640
ctacgtatga attcaggttt atttctatca tttctttagt attgatcgcg gcagtgacat    11700
tttcatttgg ctggactcaa tgggttaaca tttatgctca ccagctgcca ggatggattt    11760
caagttcaat ttatctcacc ttattaggtg tgttttccg ttcttacctt aaaagattgg    11820
gtgacgacaa tttaatggag gtaaaattat gactgctgaa atcattgaat ctaaaaacaa    11880
```

```
caacttttgg ttgaaatgtg ctgaaagtaa tttagcttcc atgctagatg aaatgggata    11940
tacacagcaa tgggtaacga gcttccaaaa aaaacgcctt atgaaagcaa ttattgcttt    12000
agctgttggt gcagtagtag gggcattgtt tagtacctgg atgatgttat tagggcctat    12060
actggctgta tttgtatgga tgctggaata tcaaagaatt gtaaatgcgt acaaaagaca    12120
tcaatttgaa aaggaacttc aattcaataa gtttattaga atgttgtttc cgttgttatt    12180
agagaggaat gctacattat acggtgcatt aaataagatg ctcaaaagaa tggatgatgg    12240
gcatgtgaaa actgctttaa aacggttttt aatcggattg agcgatgaac ctaactcaga    12300
agctcctttc cgtttatttg ctaaagaagc tagtgggacg atagagcta tgttaatcat     12360 ggctacgctt tttgattacc agcaaagttc aaatgataca acaattatta gtgaactagg    12420
tcagatgtcg agtaaacaat tatttgaagg ggtaagggaa attgctgaat ttaaactaag    12480
aaaattttat atgttcccaa caaagctcac aatggccagt tttgttccca tcgtaggtta    12540
cgcggctgcc atgatgatag atactattgc aaaattatct ttataaaaca ctgaaagagg    12600
tgtaagacat gcttgatgga gcagtaatgg ccatagggaa aatgtatatg gccattttca    12660
ttttatttgg gattttttct gcttcagctt tttttataca gatgaatcag ggaaatgaat    12720
acaagcaata tattaactat cagattgaga gaaacggcgg acttacatct tcagcaatgg    12780
atcatattga ggaatataac aaaaagtatt acgaaagccg gttcacaatt gatagtccga    12840
tgatgaatca aaaagttaag tatggagatg aagttaatta cactgtaaaa gggaacttta    12900
aaattctata ttttgacctc ccgattcaga cggtctcatt aaaaggttct gctttatcgt    12960
tgattcgata atgtagggcc ttttatatt gcgctctttt aaggggtga gggatatatt     13020 agatcaaaac gccgacagga tgtattgggt gattggtgca gtcttagtag tagggctttt    13080
aataggactt tctgtaaaag aatatccgga tatattaaac aacgttttta gtggttttac    13140
agctaaaata ccaaaatttt aattcgaata cacaatagga gagtgcaaac atgttagatc    13200
aaaacgcaga cagaatgtat tgggtgattg gtgcagtgtt agtggtagga gccttgattg    13260
gccttgctga aaggaattc cccggcttat taagcagtgt atttagtggc tttacatcga     13320
aacttaaatt ctaattttag taaataggag agtgtaaaac atgttagatc aaaacgcaga    13380
cagaatgtat tgggtaattg gtgcagtgtt agtagtaggg ctttgatcg gtcttgctga     13440 gaaggaattc cctggtttgt taagcagcgt attcagtggc tttacatcaa aacttaaatt    13500
ctaacggaag agacgtacag ctgtatgttt cttttttttt gaaaggaggc ggatcaaaaa    13560
tgaataaaga tggaccggtc gttaaggtca aggttacgcc aaaacaattg cattccatga    13620
tccataaacg ccaggcaaga ctccctcttg gttaccaggt gaccaagggg gggaagtttg    13680
acgcttactg tgatcaaaaa agtttgcttc atcaatttgt tatcaaaaac ttcactatta    13740
aaaacaacca catcttagtg aaattcacta gctgatgatt tcatcaattg aaggaggtga    13800
ggagaatggc tgctacaaaa gccgagaaaa aagatgctaa agacctttgt gaattgatat    13860
tagcgtcaca agggatttcc tatgatgatt ggcttcatga tcaacataat gcagttgttt    13920
ctaagcacag taatattttg aagaaagcag taaaacaaat ggtaagtaaa ccagcaactt    13980
cagagcaaca caactaaaaa atgcaatcaa ataaattat aagaggtgtc attcatgcca      14040
gataatattg tagatatgct tacttactta attagagcta ttcaagttgt cgtcggtgcc    14100
tacgctgctc ttaaactagg tatttacgct tatggattta tgtctaaaaa ccaacataag    14160
actgaagagg cgaagggcgg catgaaaaat gtaatcattg gtcttgctgt agtagcaggc    14220
```

-continued

```
tgtgagccga ttgtaaagtg gattcaaaac ggtataggtt tctaaatgaa agtgggggta      14280
tctaaatgat tcgagcttcg tttaaggghtg ggagaaaatt tcgatccatt attccatcca      14340
gaaaacaata cagtatacgt ttagcttcct cgaaaatggc ggaattagag agatttgctg      14400
aggaaaataa ccttaatgcg gaaatagtat taactatctt tgacgatgaa gataattcag      14460
ttctctttcg ggaatctttt tctgttggag aagggatttc gaacaaccta ctctttctcg      14520
taagcagaac attagatact acttttaaag acagtccgca ggaagaaaaa gatgcattgc      14580
ttcaaatgtt atcaaaagcc atggaagagg aagctgttga acaggaatgt aataagaagc      14640
tgttttcagt tccgaattta ggttttttta aaggcagaaa gaaaaatgaa ctagatccta      14700
aggcagccga ggcagagcgt gcccgccagg ctgaagagaa ggcccggcag gaggcagccg      14760
aggcagagcg tgcccgccag gctgaagaga aggcccggca ggaggcagcc gaggcagagc      14820
gtgcccgcca ggctgaagag aaggcccggc aggaggcagc cgaggcagag cgtgcccgcc      14880
aggctgaaga ggaagcccgg caggaggcag ctgaggcaga gcgtgcccgc caggctgaag      14940
agaaggcccg gcaggaggca gctgaggcag agcgtgcccg ccaggctgaa gaggaagccc      15000
ggcaggaggc agctgaagca gagcgtgccc gccaggctga agagaaggcc cggcaggagg      15060
cagccgaggc agagcgtgcc cgccaggctg aagagaaggc ccggcaggag gcagccgagg      15120
cagagcgtgc cgccaggct gaagaggaag cccggcagga ggcagctgaa gcagagcgtg      15180
cccgccaggc tgaagagaag gcccggcaag aggcagctga ggcagagcgt gcccgccagg      15240
ctgaagaaat tgtcgaggaa aacaaaaaag gaaaaccagc tgcagctgta aaaacgcatt      15300
tatccaatgg attcagtaaa ggaatagctt tccttaaaaa gcagaaacag tatgtacctg      15360
atcgtaaaaa taaacgtgaa atacatccgc ctatagtggc acaagaatca gctgctatgc      15420
gtgaccttga aaagcaactt aagatggcca agattgaatt gattgaagaa attaagaaag      15480
aaaaactaga attagataaa aagttggcta agaaaagaa aaaggaagac aaacataaga      15540
aagctttggc caaacgtaga aaacgaatgg cagcgcctgg gcttgggtcc tccaagctca      15600
ttttgtttgc cattcttctt attatcggcg tacaggttta tttcaacgtt gaatcaggaa      15660
atagcccgct aacagttccc ggctgggtaa ttgacattgg aaataaggtc agcaacctag      15720
tagcctctta caaaaagctt taacattgtt aagcagaaag gaggaagctt tggccaataa      15780
cgttgatcga tatgatgttg atatggaaaa gaaggcgtca ccttatctaa atgctcttgg      15840
atcggctctc agcgaaggca aaaaagagc tttaaatgaa cttaatcaag ccaataccct      15900
cctgaacaaa atctttaaca gaaaaaaat taatcaattg tccgaaaagg taaagcttta      15960
taactactgt gagaaccaag taagaagtag cgatttcaga agcaagtttt ctaaaattga      16020
gattctagct ggaagagaat ctcaaataaa tattaatgta tttgggggaac gaattgaaac      16080 agctttagga agctacttca aagaacaagg agaaaacttg actcctggaa atagtcttga      16140
agcgtatgat gagttgtata ggacaatggt taactcacaa acctttttcat ctttacgagg      16200 taataatttc acaggcagat cagaacaaga tacaagtttg atgggattta ttcttctca      16260 aaacgagtat cagaattatg tggccgatta tcgtgagtct aaaccaattc atcaaatctt      16320
tccagaccag ttcaaggaag gcatgttgga gaatgaaagt aaactttaca tcaacgagta      16380
tacaaaacat ttagcgttag ttcatgacga gaacagatct atgttgaaga atgaatcccc      16440
agattacgct gtcatcaaag agttggaagg agaaattcgt tctaatttta gtaaagatcc      16500
ggaatatccg gttattttat taaggacaat ggcagcagat aaccttaata aacagatagc      16560
aactgctgtt aatatgacta actcctttat taatgatttt tctaaagaga tgaaaattaa      16620
```

```
acaagtacct tggcctacaa ctgtgcctga acctctaact tatgagcagt ataatcaaaa    16680
taaatctaaa tatcttgaac agctatcaaa agatgatgtg ctgatgaaaa aaatgaaaa     16740 agatctgtca actgaaaggg aactagagaa taaagggact gaaaaaggaa aagttgaagt    16800
tcaaattaaa aagccctcaa atttgaaagg ttcaagaaaa gttaaaggtc tagaaagata    16860
atagaagtga ggaagccgtg tttacggctt ctttttttga ggtgatcttt tgcacaagga    16920
gtttaaacag tggaaaaaag tatttgcaga taagtatttt ttgattgcct ttacactgtt    16980
ttgttatgta gcagtgacgt gtattactaa ttttttcata catcttttaa aacagattcc    17040
cgtaatactc tcttctttta aaactttga ccagtcacag ctttcaagtc cttttagttc      17100
gatgacctgg aagtggtttt ttgaatttga ttggagtatg ggcattgttt atggagtagt    17160
gtacgttctt gcttcaattt tcatattgag acaagtgtat aggtttagaa tcgcttttcg    17220
tgatatcaat aagcaaacga aggtacagc acgatggact gagattatgg agattcaaga     17280
aacctataag gctgttaaag atgatgataa tgagtatgaa ggcagtgcag gaatgccgat    17340
tgttcatttt aatgaccatc tttacgttga cacaaactca actcataccc ttgtggttgc    17400
ttcaacacaa tctggtaaga ctgaaactta ttccctatcca tatttagatg tcattatgag   17460
agcaaaagaa aaagactctg tagtaattac agatataaaa ggtgacatgc ttaaaaatac    17520
ccgcgctgaa ttcgaaaagt acggttatga agttatgtgt ttcaacttat tgaatccgta    17580
ttggggaatg gcctataatc cattggaatt agttaaacaa gcatatttga agaaagacta    17640
ttctaaagcc caaatgcttt gtaatacact atcttactca ctgttccata atgataagtc    17700
acatgcagat cctatgtggg aaaatgcatc tattgcattg gtaaacgcct tgattctcgc    17760
ggtttgtgat ttgtgcatta agaatggaca gccagaaaat atcacgatgt atacattgac    17820
agttatgtta aacgaacttg gaagtaatcc agatgaagac gggtatacac gacttgatca    17880
tttctttggt aatttgccgc cttctcaccc tgctaagtta cagtatggga caattcaatt    17940
ttcacaaggc ataacacgca gcggtattta cacaggtaca atggccaaac ttaaaaacta    18000
tacttacgat acaatcgccc gaatgacagc tcgtaatgac ttgaatattg aggatttagc    18060
ttacggagaa aaaccagtcg cgttattcat tgtctacccc gattgggatg attctaacta    18120
cactattatt tctactttct tatcacaagt aaacgctgtg ctttccgaga agctacatt     18180 atccaaagaa agtacacttc caaggaaagt aaggtttctc tttgaagaag tcgctaatat    18240
cccgccaatt gaagggttaa atagatccct ggcagttggt ctaagccgag gtatgctcta    18300
tacgcttgtt attcaaaacg tttctcagct acgtgatgtc tacggagacg acatggccgt    18360
ggcaataatg gggaacttgg gtaaccagat ttacattatg agtgacgagt gggaggacgc    18420
cgaaaagttt agtgaaaaat tgggtgttac cacggtaatt tctgcagatc gtcagggtga    18480
tttaatggac gttcataaat cgtatagcga aagagaagaa gaaaggcctt taatgcttcc    18540
tgacgagcta agaaggttga aaaaggtga gtgggttgtt ttaaggacta aaaaacgtga    18600
ggacttaaaa agaaatagg tagttcctta tccgattttt gcttctttag ataacggaac     18660
aaatatgctg catagatacg agtatttgat gcatcgtttt gataataaga ttgctcttgg    18720
tgatttaggg tttagaggag agcatgaaac actggatctg gaaagcttat tgattgaatt    18780
tgaatttaat gaacctgtga aggaggaaag aaaaagtaaa ccaggtaaag ggaaaaaaca    18840
aaaagctaaa aaggctcctg gtgaacctgt ttcagtgaa ttcccattgc ctgaagaacc     18900
gattgggttt actgaatctt cagagggaat ggattcacta ttcgcctcaa ttccagttga    18960
```

```
gaatatgaac gaacatggat tttatgaaga tccgccaatg aatgaatcat tacatgaaga    19020
tgatttagaa gcaagtgagg aggatattat tatgaattca cttgaagagg tgtacgaaac    19080
gagtacacct atttctgatg caattaaacc tgatcattac gtgtatataa agttacttgc    19140
tcataagcaa ttatctgaaa gcgaatatgc gtatttcgat agtctgaaaa cagttgagga    19200
attaagggcc ttttttagag cgccagagaa aaagaaatt tatgaacaaa ttaaaacaca     19260
tatagagtaa gtgagggttg tttatggatg attcagagat tctgaaaata ctgcttaggt    19320
ttcaagatta cctatccctg acttcaattt ggaccgcacc attccgagtc atcggatggt    19380
gggttattat gggcctggcc gcaattgtag atgccctatc tggggggatt gaagagattt    19440
atgatttgct taatttcttc gatagtgacc aaattagtgg ctttatagat aagtggatgc    19500
ctgtcatttt tgcattaatg gcattggcgc ttggctttct tggatggaaa atcatagttc    19560
agaagaaaac tgattacgac aaaataatca caaattcatt atttgcttta actcttttcc    19620
ttgtactgcc atgggggatg cagcaggcgt cggatctctt gcttgctggg aaaggaatgc    19680
ttgatgaaga cggaaagctt agtgtttcca ctaaaatata tcaaaacaat atagtcgatg    19740
tttataaaat cgacaaggat gctgagtgga gtaagaaaga attcaaaaag ctaaagaaga    19800
aaaataatat cgagaatgac gaggatgtga aactttttaga tataacgag ccagttgata    19860
caggtggaat ttttcactct agtccgttaa ctaaagatgg cgaaaaaata ttagataaaa    19920
aagtaagcga tgcatccgga gagaagaaat tagaggatct tgagtcattt tggatacaag    19980
atgatgaagc ctattatcga tattcttggc acccttggta catgatgttt gaacttggta    20040
ccatagcatt tgttttattt atgaccatgt ttaagacagc gcagttaatc atggaactag    20100
gaatcttaaa gattttcagt gtaggaactg ctttaacgga tcttgaaaac ggtcaacgta    20160
ataaaaagtt cttggagaag ataaagaata cttttcattgt cttattttca atcgagcttt    20220
tgttacaatg ttacatcctt tttacagatt acattggcca agctgacata tctgcaccaa    20280
taaaaatagt tgtattgatt gcagcagcta ttttaacggt ggatggtcct aactttatag    20340
aagaaatgtt tggtatagat tctggattga agagcatttc gcggagttta gttgggctat    20400
ttgcaggtgc taaaacagca aaaatggcta cggactttac ggcatcaaca gctaaaaagg    20460
cggggaaaat ggcaggcaaa attgccaaga aatcatctga tgctgcttta gttggtatgg    20520
gtgctggaaa gggtatactt gatggtttta aagagaacat ggaagctgct aaaagtggtg    20580
gaggaagtaa cgggggaaa attggaaaag acggtgacac gcctttgtca catggattag    20640
ccggtaaacc gactaatgtt atgtcagacg atgctttaaa agaagcaatg atgtctggtg    20700
acgatcagaa agagaaggat aaatcgtcac aatctgattc tccgttgtcg tcttttgaata    20760
aagaaaatag ctccgattca tcaacagagg gtatcgaaaa tcgcgatgat agatcaggca    20820
cagaaaatgg atctccaatg gaagatcata atacaccact atcatccatg tcttccgaag    20880
aagaagctgg aagcaacaat gagaaaggat cagacaatat tctatcaaaa gatggagata    20940
caccattaca agcatcaaaa gatcagtcga gtcctgatgc agctagtgat ggtctaggta    21000
ctcagcaagg taaaaacatt gaaatggcca ctgacaaaga cggaaatcaca ccgttgtcta    21060
atatggcatc atctgaagga atacaacctg atcaaccagg tggatctgct gctgacaaag    21120
acggagatac accgttatct aatatggcat catctgaagg ggcacaacct ggtcagtcag    21180
gtgggactgc tgctgacaaa gatggaaata caccgttgtc taacatgaca ggggaaagct    21240
cagttccagg acaaggcggc ggaaacgcgc caggaagctc tgatacgcca ttatcgtccc    21300
aagggccaac aggaagtcca attccaggac aaggcggcgg aaacgcgtca ggaagctctg    21360
```

```
atacgccatt atcgccccaa gggccaacag gaatcccagt tccaggacaa ggcggcggaa    21420
acgcgccagg aagctctgat acgccattat cgtcccaagg ccaacagga atcccagttc    21480 caggacaagg cggcggaaac gtaccaggaa gctctactaa tacgccattg tcatctcaaa    21540
taccacctgt aggaccaatt tctagtcaga tcggtggaaa cacatcagtt acacctggta    21600
gacaattgtc tcaggggccg attaatagtg gtctcacagc aaacaatagc acttccaata    21660
atggatggga ttcgttgttt gcgactatgc cacagaatac aggttacat tcttcaggaa     21720 gtcttatgcc gagcagtcct atttcacagg cggcgccggc ttcactgaca cctgttgcac    21780
caagcagtaa tacatcgata gtaaattccg tttcaaatgg ttctaattca acttattcgg    21840
cgcctacacc ggcaagtaac attttgccaa cccaccgcgc tgccgtagga atgttttac     21900 caacctatag agcacctgta caaaatatgg gaggtggccg ttttgattac tcacctaaag    21960
gagtgagtac agtaagcaat aaaccgattg gaatgcctaa acatgttcaa caactgcag    22020 aagcatttaa aaatcagatg acaaaaaggc caactacgaa tatgactgca aaggatgtct    22080
tggttaataa gtatgctgac ttggcgcaac ggatatatga ttcaaagtca gtaagaaatt    22140
caaggacagc ttacgatatc gcaaaaaaca ctgtaaatac tggattcaaa gggggactg     22200 ataaatgagg caaaccgtat cagtaccaga aaatattcaa gcaaaatac aatggaataa     22260 actaacggtt gtggatggtt ttgtgattat tgggagtttg gctgtcgggt atttcatgaa    22320
aggcttggta tacccgtatc ttcagatacc ttttgtatta tttatcgtgc ttgccactac    22380
attttatctt tggccgtgtc ctgattcacc aagtaaaaag atttatgaaa tgacgctcat    22440
ggttttcaga aaggatagtc ggacatataa agcacaagag cctgtcaatt attccatgat    22500
aaagcaggag gattaaaatg ggttttgatg cactgtcagt taaaaagaag aatcaatcag    22560
gaagtacacg gaaattaaaa aaaatacaaa agagtattga tcgaatcaat cgtgtatatc    22620
cggtatgtgg atatactgat gagggttatg taaaaacaaa atttggacta aaagaaggct    22680
actttgaggt atttgacgtt aaacattatg acaccaatat cctagacgaa aaagagttta    22740
actttgtaac agagtcctac tggaaactac agcaaattta ttcagatcct cttaaagaag    22800
tgcatatgaa tttgcctgaa gataatcagc ttcagcaaga atatattaaa tacaaaattg    22860
aacgaacaaa taacttttgca aggttgagag tattaaacgc tgaactcgaa aagttgaaat    22920
tcatagaaaa aacatataaa agtcgtcgca cgtacctcat tgtctttgga agaacagcag    22980
aagaacttac taaaaggatt gacgatttaa ctcgctttac aaacttttta gaaccgcagc    23040
cgatttctat cgagaaaaaa attaagatct tacatggtat gaataacttt atttaggcgg    23100
tgaatggata tggaaaaaat tattaaggat ttagattttg tgtatgccac ccaaccaatg    23160
ggtggcattt cttttaagga tgaattttt aatcgtacag gtgatggata tgttgcttgt    23220
ctccatgtat accgttatcc ggaaaatttc acaccatact ggttaaacaa attaactagt    23280
attcataaca caattgttac tattgatacc tatacacaaa aagacatcaa ttatactgat    23340
aaggtaaaaa gctcgactaa tgaaatgaaa tcgaggatac gtaatgcagc taatgaaaca    23400
gatgcagatg tagctcgtga agaattgcag actttaagag aactcggggtt ggctattacc    23460 aaaggtggag aagtaattaa acagattcac gtccggatct ttttgcatgg tgccacacaa    23520
tcggaattag aaaaacgtat atctgaagtt caaagagta ttgacagtga tggttttaaa      23580
agtaaagtgt ttcttgatga aaataaagaa gaatggcaat ccttatttct tgattatgaa    23640
actcaattaa ccatgccaaa caaaagaata ggaaatgata tgcctgctga ggccattggt    23700
```

```
ttaggttttg cttatgatca aaccagtcta agtgatccaa caggtgttta ttatggttat   23760
acatcaacga gaggaacagt ttattgggat ttgttccata agacaactaa aaggctatat   23820
tataacatgt ttgtggcagg ggatatggga tcaggtaagt caacacttct aaaaaagatc   23880
ctaagagata atgcttcaaa aggtaacttt attcggggct ttgataaatc aggtgaattt   23940
caatccgtta cggctgatat gggcggaatt actattgatt tggatgggag caacggccgt   24000
ataaatttaa tgcagatatt cccgtctgtg acaaagaaaa taggggacaa agtcgtaata   24060
gacgaaagtg cttcttttag gcagcatgtt tcaaaattaa attcgtgtta ccgaattaaa   24120
aaccctaaat ccgatgataa tgttttagtt caatttgatg aattagtata tggattttac   24180
gagaagcata acttttgggg agaagatgca cgctccaata tcactcaatt acctcctgaa   24240
gaatatccat tattatctga ttttcaagca tattgtgaag aaagatatca tgcagaaaaa   24300
gatccaaatt tcaagtccag aattggcgac atagctatgt caataaagaa ccttgttact   24360
caatttggag agatatttga tggtattact actattccgg atatggtgaa tgaacagatc   24420 gtatttacg acatcggaaa cctgtcacag ctgagcgatc aagtaaagga tatccaaata   24480
tttaatgcgc tcagtcaaat ttggggtacg atgatgaata ttggaagaaa agaaaaagaa   24540
gcttatgata aaggtaaaat acattggttc gatattacga gattccttat tatacttgat   24600
gagtgtcaca atttgttgga attgaaaaaa gctcacaccg cgaactttt tgttactctt    24660 atgtctgaag cacgtaagtt cttggtggt ctggtattgg ctacacagcg tattgaacgg    24720
atgtttccga ataccaatac ttctgatcca gatatggcta tagcagcaaa taaacttcgt   24780
gaaatatttg ggttaactca gtataaagct ctgttcaaac aagatcagac ttcaatgaaa   24840
ttaattaaga atttatttga agaccaaatg acagacaatg agtatgctct gctgcctaaa   24900
tttgaaactg gtgattgtat tctttcgata gctggggatc gtaatttagt tatgcatgta   24960
gaggctaccc aagaggaact tgaactgttt gaaggtgggg cttaatgttg aaaaagattc   25020
cggcaaatga agaaaatgca gaaaaaaaga ttgttaggca aaagaagctg tttatagtca   25080
tatgtattgt ttttattggg gctatgctgc tttatttat gggcggaagt aataaagaaa    25140
aggtaacaaa gaatgaacaa aaagaaagct taattgaagg aatagttca gagcaatcaa    25200 cctacaaaag ttctgtcgtg aaggaagaaa aagcagagga taaagataaa caagaaatgc   25260
aacaaacact gaaatccttt atagaatcat attactcgta cgattataaa aataaagaca   25320
aacatttaaa ggagtcaaaa aaatatttga ctccggagtt ttataaggaa ttaagtcttg   25380
ctgaagaaaa caatacaaaa gtgcagcctt tcgcttatcg aaaagtacag gacatttctt   25440
attcaggctt ctctttagta aacggaaagc ctcattggat tgccagtgtt aatgctgaat   25500
tattggatga taagaggaag gtcactggca ctattgaagt tgaatttgaa ttggatttaa   25560
acaaaagaga agataattgg accgtaacat attttgctgt aacaggtaaa gggttgaaag   25620
agaatgaata acggggcatc tgccgccaaa gaagcagtga atacttaat taagaaacaa    25680 ttacagaagc gcgcgcttct gttttttta tgctcttggg ccggtttaat tacgattgta    25740
gtatgtgtag ttattgtctg tgcgataggg ataatttctg gcctatcagg ttcagattcg   25800
ggcggaggcg gcggagaatc tgcgataaac attgcgccag aagttgaaca gtatagggca   25860
gttgtagaaa aagaatgtaa agcgaatgac ataccagatt tagttgattt aatactagca   25920
ctgatcatgc aagagtctgg tgggaagtca ttagatgtaa tgcaagcaag tgaatcaaaa   25980
gggctgcctc ccaactcaat taccgatcct catgaatcaa tcaaagtagg tgttgcaaac   26040
tttgcttcag tatataaagc agccaaagca gctaaaaaaa atgtcaaaga aacggcgctg   26100
```

```
caaggctata actttggaag tggatatatc aattgggcga taaagaaaag tggaggttgg    26160
acaaaagaaa acgctgctga ttttgctcga attcacagta acggacagca gcgcccaaac    26220
ggaacttgga tgtatggtga tcagctgtat gtagagcacg ttatgaggta cctaaagccg    26280
aataacggtg aaaatggtgg agaagttgag gtaataaagg gtggaaacaa agttattgag    26340
aaagcaataa agaaggctc ggcttatata ggaaggtcca cttatgtaat gggtgggggg    26400
agaaatcaaa gtgacatttt aaaggggatc ttcgactgta gcagctttgt acattatgcg    26460
tttaacaagg caggtttatc ccttggaaac ttagcctcta caacaacaga tacgcttgtt    26520
gtacgcggaa aaaagtcaa atattcaaat attaaaagag gcgatttagt attctttgat    26580
acttacaaag taaacggtca tgttggaatt tatctcggga atggagagtt tttaaattgc    26640
caaaatagtt atggtgttag cgtggcaaag atgagtaata gctattggaa aagtcatttt    26700 aatgggtcg tcgtacgtat tacagagtaa aggagggaa ccgaaaaagt gaaaataaaa    26760
tttaaaactg tcggtgcaaa atataaagtt tctacaggtg ttattgccat gatcctgctg    26820
tttttcttgt ccagcagggt cattttgat tcgccgtttg aagaagaaaa tacaaaacta    26880 aacaccccg ttagtataaa taacatgact gtggaaatga cggatcgaac ttattttca    26940 gacaatcaca tgcttgaaat tgatttgatg atcacagatt ctctacaaga tattcctcca    27000
aaattagatg caattgttaa ggaaaaatca aataagagaa agaaatatca tcccgaaatc    27060
atcaagattc gtgatgattt ttatgtgttg tttgtaagag atattccgga agattggaca    27120
gcagtttcgg ttcagctgac tgatgaaaat gatgaagatt caagctcaat cgggtcgagc    27180
aaaaagatat attcctcatc tgcagatacg aaaacaaagg atgttttgt gaaagaaat    27240 caggattatt atgaagcaaa atatatcgat ttaaagatca aaaataataa aaaattgatt    27300
caagaagaag agaaaaaaca gaaagaatat gcggttgaaa ttactcaaat aaactctcga    27360
atctcgtctt taaagaaga taaggaatac cagatcggta agaaaaaga ggaaacagaa    27420 tcacaaattt catccaatga aagcaaaatt tcttcaaaag aagaggcaat aaaaacgagc    27480
aaagaaatgc taggtgaact tgaaaaacgg aatgaattat tgaagaaaag aaagagcaat    27540
ctcgtcatcg aagactaaaa aaagaaacac ttatttgaac agatcgttgc aaagtaatgt    27600
gcagaaatcg atgaaagga gcgttaacaa atgccggatc tcaacatcaa aggtctttca    27660
aaagatacaa tgaataggct tgcggataaa gcgaggaagg caggactttc tcagcaagaa    27720
tacctccgcc aattgcttga taaacatgtt gttgcggatg aagttgaggg cgtgcgaagc    27780
gaattaggag aagtcattaa atctgtagca ttcgccctcg aacaaaacac caaagtactt    27840
aacgaattca tcagagtaaa tgaaggatag cgaccgattg aggacgctgt ccttatttct    27900
ttttaaagca gcaaataagc tggccgcagt gtttaaagcg caaagtcttt tctttattaa    27960
agaccgtctt taaaagaag gaaaaatgag ctgcaaagat cattttgtgc tgtcatgtgt    28020
aaaaaagata ttgaaagtg aggttagat atatggcaaa agtaaagaag catcttacct    28080
ttagtggtcc gacagaatca ccgtatggta ttgcttatat tgaaaagaa atgaaagcga    28140 agaattgctc aaaaatgaat gaaacaattg aactgatctt tgctgaacac gatgaaatga    28200
aagcgagatt atcagaacaa gatgcacttg tcgagaaaat atttcagcgt tttaagaaga    28260
cgcttgacgt tatccgtgtg cgcgccggac acaccgataa aaatgctcaa attaacttag    28320
agctttggaa tgcatttctc atggccaacc cgttacctgt gacagtttta acggaccagc    28380
atacctctga gtcagtatcg atggcaaaag aaaaagttag taatgacatt gctacattta    28440
```

```
agcaaaggaa agatgaacag aaggctaagc aggaaatgca gaaaggtgaa aaataatgga   28500
ttctcctggc gttgtattag tctctaaata tgtgtcgggc aaatcaacaa aattttcgaa   28560
gtatgtcaat tatatcaatc gtgatgaagc cgtccgaacg gagaaatttc agacttacaa   28620
tgtaaataaa ttagacggat acaatcaata tatggggaac ccggaaaaga gcagcgggat   28680
ctttacccag cacaaagata gcttatcacc agtagaaaaa aatcagctga aggagatttt   28740
cagacaagca caaaaaaatg attcagtcat gtggcaagat gtcataagtt tcgataacaa   28800
gtggttagaa gaacgcggga tttataactc gcaaactggc tgggtcaatg aagggggcaat   28860 tcaaaactct attcgaaaag gaatggaagt tttattaaga gaagagcagc ttgaacaaag   28920
tggcgtttgg tccgcagcca tacattacaa cactgataat atccatgtcc acattgcgct   28980
agttgaaccc aatccgacaa aagagtacgg cgtctttacg aacaaaaaaa caggtgaggt   29040
ttaccaggct cggcgtggga atcggaaatt aaaaaccctg gataaaatga aaagtaaggt   29100
tgcaaacacc ctcatggatc gggacaaaga acttagcaaa atatcacagc tgatccatga   29160
tcgtattgct cctaaaggac ttaaatttca gcctagattg gatacataca tgactaagat   29220
gtataaccat atctacgaaa atctgccgga agacatgagg ctgtggaaat ataataacaa   29280
tgctttgaat aatattcggc cggagataga cagtgtgatt acgatgtaca ttcaaaagta   29340
tcatcctgaa gactataaag agctggatca gtcgttaaaa gaagaaatgg aattcagaaa   29400
atcagtatac ggagatggac caaaacaggt agagagatat aaagagtata ggaaaaataa   29460
acataaagaa ctctacacta aattagggaa ctccatgctg aaggaaatgg ccgaaatacg   29520
taggcgtgag tcgcaatcaa aacaaatgaa tcgctcaggt acctatgctc ctagttcagt   29580
atcaaataga caatgggata caagggtag gcgcataaaa agatcagata tcaataaaat   29640
caagcacgct ttagataaag attatcagag catgaaaaac atgcgtaagt accaacaaat   29700
gcagtatgaa atggaacaga gccggtaggc aattctgaaa ttaaaggaga ggaagccaat   29760 gattttaaa ctagatcact atatcaatga agagagagat ccagattatt tgctttttat   29820
cgaaaaggac attgaacctt cccgatttga ggaagagctt ttaaagctta tagagataat   29880
tgggtgtatt catttagat ttgagcagct tgttagggat gatatttgtg tggcaggaaa   29940
agatatagtg ttccttcttg agaagtatta tggtttcaaa aacgtaacgt ccgaatacat   30000
gttgttagaa aaagaaacaa ggctgccgcg tgaggaatgg tatgtttta atgaattcag   30060 agttggcact aaccaagtgc ccgtgtttca aatagatgta tataaagcgc gggaagcatg   30120
ctgcggaccg gaatacagaa atctcatgat aaacaggctg ccacttgata aggaattcga   30180
taatgatatt gaaaagctag gagcttttta tgttggtgaa cagcattaaa aattaaagaa   30240
aacacatgtg agatcaggat aaatcctggt cttttttta tgactataaa aggggggagtt   30300 taaatgccta gagtaagtga agatgtcata aaacaagcag ctgcagttga tattgtaggc   30360
ttctgtgagg ccaatggtta tgagcttgtt aaattgagcg atagatggta tcagggcgct   30420
gaacacgata gcttaatgat tgataaagag aaaaacagct ttcagtggtt tcccagggg   30480 aagaacggca attcaattga ttttgttcgc acattttacg gaaaaagctt ccgtgatgct   30540
gtatcaatgc tcactgaaaa agactataag catacaaaag aagttaaaga gcagccgcaa   30600
aaagaattcg tttatgacat cgttcatgat aactccacag aacaagtcga acgttacttg   30660
actgaagaaa gaggcatcga taaggaata gtaaatgcac taatagcgaa aggattactg   30720
agacaggata aaagaaaaaa ctgtgtgttt gtttgggga atacaggcaa gcgtgtaggt   30780
gccgatcttc agggtaccat tacaatgaat aaagacggaa agagaacgac atttaaacaa   30840
```

```
attaacccca attctcagcg gaattatggc tttaatgtct cattaggcgt ccctaaaaaa   30900
ctttattttt ttgaggcacc tattgatctg ttaagttatt ggacaatgta taaagaccaa   30960
ttatctaatt gccgtctcat ttcaatgaat ggagtgaaga aaaacacggt tttcaacctg   31020
ataaagcata caatgaaatc ccgtggtgtg gctccgacag aaggagtata cttcggagtt   31080
gataatgacc atgctggcca caaatttatg gatgaaatac gacaatatga gttttctgtt   31140 aaagggggagg aagtcaaatt tcataactta atcccggcag acaatcatat tcccaaagaa   31200
tatttagaac tgtatcaaac atacggcagc caatatgggg tcgattggaa gtacctagct   31260
gctattcata aagctgaaac gaaccttgga aatacaaatg agattacgaa cggttatggt   31320
tttggcaagt attttggtgc taaacagctg cctagtgaaa aaccttatga gatccaggtg   31380
ccaatagcaa tagaagaagc tgccagggcg ttaaaagcta acactataga tggaaaaact   31440
gatataggat cagttttaaa acaggatgta aaagaggttg atctgactaa tcaggtgaaa   31500
atgcaacaga aagtacaact ttattacgac aactataatg atctaggata tctgccggtg   31560
gaagaggttt ctaaggattg gaatgatgtg ctgaaggtcc gtagagctgc ttcaaaacat   31620
cgcgaaaaaa cacattctca aaagcaacat aggagcaaaa aaaatatgct tgttagggg   31680 tgataaaaca ccgatttacc tgaattaatc aagggaaaaa aaggctaaaa ggtatcttca   31740
gtatcgctaa aatggtataa tatattatag agaaagggag gtcaattgta tggaaaaaat   31800
aaaaacaatt gagcaagctc gtgagaaaat gaaagaactg ctggctgacc cccaatataa   31860
tcgtccggag aactacccgg aacgaaacgc tgacgggact atcctgttag atgaaaataa   31920
tgaacttcac caggaattaa gataattggc tgaaacagat ccaaaaaaat tagagctagg   31980
caatatacat ttagcgataa ctgaatttag agatgggaca ggtcgtaaag cgcggcctgt   32040
ccttgtttta ggttcaaaga aatccattga aggtgctttc gagcctgaag tcctgatcgg   32100
gtacatcaca tctaataata acaataagaa tttctccaag tttaagtatc cgattgctga   32160
ctggaaagca gctggtttgg ataaggaatc atgggttgtt ttgcaggaac gggaactcaa   32220
atggatgaat cacgagaagg attttcttaa acacatcgga ttgctgacgg aacgtgatac   32280
aataggcgtc ctgaataaat ttatggaagt ccgagaatta gaacagtcat taaagcaaga   32340
ggctgaaaaa tctaagccgc aacctcgaaa gggtaagatg caagtgacta ttcaagagaa   32400
tcctacattg aagcgcagta gtccaagcgc acaacgaaga aacagcagag aacggtaatt   32460 tttttttgaag acaagctccc tcacttcagg gagctttttt attttctta ttgtattaaa    32520 tgctgccggt tgcggaaacc caggaagcca ggtgcgttgc gccgatgatg cggaagctga   32580
agaagtgcca gtgatccagg agcgagagga taaataactt atagagctga atattctcgg   32640
acacattctt tcagctaaag aagggagata aaaagttggt aaataaagaa gtaagtataa   32700
gtgatgaaca attaaagcgt atagggctag acttattaaa ttttggtctc gtatatatcc   32760
gttcaatatc aggtgctgga cattttccta aaagggaaca agcaatagta aatgatgtgt   32820
gttataggat gtcggatgct ttgcataatc tccctgagca cttaatttat tttaatcgct   32880
tgttaatact tgacgaatta gagaaactgg cactaaccgt ttctcgtatt cctaaaacaa   32940
atatagttca aaatccgact ctacagttaa tagttgaaaa aataaagctg ttgtctggag   33000
attcttgttg caacactcaa taacaagtgc ccttatttttg ttactttttt tatcattttg   33060
ttgtttgcat tgcaaactga atatactgag tatatactgg ttatataatt tatacgttag   33120
tcatctatat gatgaccaat gtaaaaaaaa cagatgtttt tgcataaaaa aataccggag   33180
```

```
tgcgccaaca ctccggtctg tacacaagct gtccttaagg ggctggctcg agtatttttc    33240
ctaatagact tatcccttta acttttccag agctcaaggg aggtctattt tttgtttttt    33300
aaagtcaaca cggcaacaat taaagagccc aaaccaatta atgatgattg aagctaata    33360 aataccatta gagcttgata agcttcagtt gacattttat cacccccttt caggggccag    33420
cagatcgcta ttgagataca cggcaaatgt acaggaataa tatacactag acaaccatat    33480
tgtggttgtc ttttttgta tcttaagtat agcaagctat ggcaaaaaca caatatatag    33540
attagtgttt tcacaaatta aagaagcatt tctcactttc atataaagac aataagagct    33600
tctcatctat ttattttagc atggtcattg tcccaccgta taaagttctt tataatttga    33660
tcttctttca agactgccga tatctttaga taaaggagag atataaatgc ttacagaaag    33720
acaagcgttg caagatcgtc tggaaaaaat agacaaagat gaaatcactt tgatcaagga    33780
gtatcagaaa caacgaaatc agattttgtga gcgtcttaga gaaatcgata gagaagaata    33840
taaaaaccct cctgatctta aacaattagc ctcgctagaa attcatcaaa agtcaaaacc    33900
tgaaagagac ataagaaaac atgttgccgt taatattttg aaagtcaatc cagacggttt    33960
gtctgctgat gaacttagga gtaagattga gaaagagaca aatatgcaaa tacttaacat    34020
gacaaatttt atgagatcaa ttatggagaa aaatccttca gtaaaaaaac cacgaagagg    34080
ttattataga ttcgaagaaa tgtaacacaa tgttattgtg ttacattttc aaaagagtgc    34140
taatccctta tgtaccaagg ggttagcact cttttttttt tgaaaagttt aaaataaagt    34200
ataaaaatgt aacacaacat atgttataat gatattgtgt tacattttca aaagaggaa    34260 aaggggtgaa aaaatggatg ttcagtattg ggaagtgaat gttagtcgta aagaagctgc    34320
taccaggatt gcggagaaac ttaacaaggt taagtttttg tttgacgctg ggatttctga    34380
tactccaaga ggaaagtgtc tctacataaa atttgatgat tggcacctgg aatataccga    34440
aaaaacaaga aatggaatga tgctttttct caatcagtta aatagcatga taagagataa    34500
atcattggtt gctgggttta taatgatct gaacattata gatttggagg ggaagattaa    34560
atgttgaata gagtagttct agtaggaaga ttaacaaagg accctgatct tcggtatacc    34620
ccacatggaa caccggtcgt cacttttact ttggctgtga atcgtacatt tacaaaccaa    34680
tccggtcaac gtgatgcaga ttttataaat tgtgtggcat ggagaaggac agctgagaat    34740
gttgctaatt ttttaaagaa aggcagtatg gcaggagttg atggccgtct tcagactcgc    34800
acttatgata ataaccaggg gcaacgtgtt tgggtaactg aggtgttagc tgattccgtt    34860 cagttttttag aatccaagaa caagaatcag aatgagacca accctggata cgatcaagga    34920
tttaaaggtc aaagtaacag ccgggaaggt tttgctgatg ttggtgtggg gagagatcca    34980
ttcacaggtg gaaagcctat tgatgttagt gatgatgacc ttccttttta atgacacgaa    35040
aggagaattt agaccatgag agaatattta tcgtttaccg gtatttgcat tgcttttcta    35100 atgttttttgt atgtgggttt ctattggatg gtacatgaga ctgacgagac ccttacaaag    35160
atggataaag atatcaatag tcttatagaa aaggcagcta agaagcaag aattgagaaa    35220 gaaaaagtgt taagaagggg gaagaagctg gatgctttag tgattgacaa atattctact    35280
acagattcga gtatggattt taccgtaaca ccgttgtta taggtggtgg aatttatatg    35340
atgtctggag ctacaccagg agtaacaact gagaattatt acattaaaat ttatgcagac    35400
gaaaaaaatt atgacataac tgttcctaaa gaagttacg atcaaaaaca agttgggcta    35460
agaataccga ttaaacttta taaggataaa atcgaactac tataaccctc cgggatcagt    35520
cgccaaacag gaatcccgaa gagttaagga aatggggctg cttcagccct taattaagta    35580
```

```
taaattatta agcaatcgtt gaaaatagga ggcgctgtta tggaaagaaa agagaaaaat    35640
tttttaggat ttaccgtaag tattgttgtt ggtgctattg tggcctcttt atgcataatt    35700
caagcgattt tcccaaatga atttaaggca ttcttcattc aacattctat tttctttaat    35760
attatgggtg gattccttgt atttattgtt gccgtgatac tagggtttgt aacctttata    35820
aacggaagat actaacaggc ggggatattg aaaaaactgt tcaactaaca gcagcactat    35880
tacaatagaa gtaatgcaaa aaggactgtg aatttagatt tcacatgact taatttaaaa    35940
cgaagaggta atttgtatga atttagttga accgatccga aacagaaaag atatagacaa    36000
catgaaaaag ctactttatt cgatgaatga acgtgacgcc gtatatttca ttatcgggat    36060
aaacactgct tttcggatta gtgacttaat tcatttgaaa ttcaagatgt ttattgacga    36120
aaaaatgaag cccctagatt actttgaatt gagagaaacc aaaacaggga aacacaacaa    36180
aattgccatg actaaaggtg ttcgaaaagc aatcgttcaa tatgttcagc accggtatga    36240
agggaacctt gaccattacc ttttcaccgg ccagaaatct aaagataagc cgattaccag    36300
ggtgactgcc tggcggaata ttaaggctgc agctgacaca ataggcttaa aaaacattgg    36360
gacgcattca ttgcggaaaa cctttggtta tcatcaatac aagaatggaa ctgatattac    36420
gctgctgatg gatatgttta atcatagtag cgcgggcatt acattaagat atatcggaat    36480
tacacaggac caaaggatc aggctgtgaa gtcattagac ttatgatttg actactaact    36540
aacaggggga attcatgatg tcaaaaaaaa taaaatacat gttcgccatt gcgctggtga    36600
ttacgctaat ggttttattc aggcatattt tattccttct gttggtgaaa atggtcttcg    36660
gcgctttact gattttcgtt ggtattgttg gtgtgtatgc tctatttaga ttatttgcgg    36720
gattaataag tgtggcactt gtggtcgcag gaatgtttct tatttttaag atcgttcaat    36780
tggcttgtgc atagaaagga gatagcatgg aatatttatt attactaaca tcattgttac    36840
ttttgccttt agctgcatgg ggtccagaaa tttttgatgg tttaatgaat atctccaata    36900
aaatttctga tatgagagag cttcctaaga agtacaatac gagtaaaaag ttaattagag    36960
attatttgaa gatacaaaaa aatttaagtc ttaaaatgga tgctatcgta tatcgcccaa    37020
acaaggatgt aagttttacg acactggtgg ataatcttaa agatctgttg gatgttctta    37080
gattagaggc tccacgcttt gatcattcta ataagaatga tttattggta aggaattttc    37140
ctcaagctta tttaaagta tacattcagc ttatacgcta tgatgactct ttgaaaataa    37200
tatttgatca attgatatct ctaatctatg gtgattatga tgaccccat ataaaggaga    37260 ttaaagctct tagagatgaa gtgacggata ttatcgtgtc aattagaaga gaagccgaaa    37320
acacaattaa accttatcgt agagagaaaa acgaattatt taaagtcaat gttaaacatg    37380
ctaaagaaag aattgaattt gaaaaacagt tcataaaaga gcaacgcgcg ttaaataatg    37440
ccggctcaat tgagttgaat aaaatataag atcgttctta atgacgcgta ttgcagtgga    37500
tagtcaatct aatgaagggg tttaagataa tatgaatgag acattgttta atatatttgc    37560
aggattgtct tttatttctc tgttgttaag cctatttaaa aaatttgaac gtgtgtttat    37620
ctctatagga gcaatatttc taataatggc atttagtacc ggagggtttg gcgaagcact    37680
tcgttcatgg ttaccagttg atcaagatgt acaaaatcaa acactctcgg ttataaaaac    37740
attccgtatt cattttata taatattgtt ttttggaatc ttgggagtca ttatcagtct    37800
atttgttcgg cataaaagga ataattctag tgtaagtgaa gaggagtgaa tttgaaattg    37860
aatttaaaaa aagttatcgg ggtaatcctg atgactttt ttgttgatta atttcctata    37920
```

```
gagcaatcaa gaggtataat tttcaatatg gaagtgagag ggggagagca cgctggttat    37980
tgataagacg agaatattta tcagttcagc atacgaagag tccttaaaga caccgagaaa    38040
aatcatcaaa aaacacttag aagaatgtgg ccatgaggta cccatctttg aagaagaaga    38100
ttttggaaca tggaagccgg atacaatgaa gcattgcatc gaagtagttg agaaaagcga    38160
cattgtcata ttactgataa acactaaatc aggtgaagaa ccggaattaa gatgggggaa    38220
tgtaacacct acatacttgg aattccaaga agcttggaaa aagaagaagc acattttggt    38280
tttcgtaaat ccggatatca aaaagaggtt ctttgaatta aaaaaggatt ttgactcact    38340
atataaccaa tatattgaag agaaccatag gccgcctgat tcacccttttg atcctttcga   38400 aaactggatc gccagtcagg atggaatggt taaaagacat ttagaagctg ctgatccttt    38460
tgtttgggca tttttatatg acatatatat aaaaaggtat tggttgtatg aatttgatta    38520
tgcacaatcg gaaaagagg ctaaacaaat tgctcaaatg atcagcaatt ctttaaagac     38580
ggttgttgac tttatcccta ggttagcgac gttaactgag attgaagagc agcagtcata    38640
tttagtagaa tacgccgaac acacccttac tatgctccat caaagaaatt taatattgaa    38700
taaagagcaa caagattggt caaactttt aaaacaaggg attgaatttc ttaaccacag     38760
ttacgaaatc atacaggcta aagatacaaa cccagtagtc gttaatcata tcaattcatg    38820
ttatgctgct tcgttatatt ctcaggatgg agaaacatta agattggtcg gaaaagcagg    38880
agatataaca gctccggaag tatttgcatt atacgaagag ggaattcatg ttgttgatgc    38940
cttcaatcaa ggtgaacgat taattactta cagggaagat aaaaagacat tctacatcac    39000
tgaggccatt gataactttg ttctatgcct tcatttttca cttgaagagg attggaatgt    39060
aaagcgtgct gaagcatacg cacaagaggt tgaatgtgct ataatggata aacaccaact    39120 ctatttgaa tttttgaact tgctgatagg agggagcact aatgagtaga gaacttgcga    39180
attacagtag ctctggctcg gttgttgtta aacgttcccc agctgtaagg gcaagaaaag    39240
ttaaaggttc tgccggaact agggctagaa aaattacagc cgatggtaag tatattcctt    39300
ctcaaaatct aagaagaaca atttctaaaa tgaattcgaa tgttcggtct ttaaatgatt    39360
tattgaataa gtcaaatcaa attaaatcag atcaggaaaa tcgttaaaat agtaatcgtc    39420 cttttttatta aaggacgatt ttttgtttat aggcaggaaa agaccgtgcg tcagtatcct    39480
ctatacagct gaaggtaaga tccggccgca tccggaatcc aggaaagcag gcgcgctgcg    39540
ccggtgctgt ggcagctgaa gaaagaggtc gatgccaggt atcggagcac ctggaaatac    39600
ggtgaggccc gcgacatccc caatcttata cgttagcgac attgaaaatt tccgaagagg    39660
gaggttgaaa cgttgataaa gaaaggtttt cgtgattgta acagtgtaac aggtttactc    39720
gttaacaaat ttactgtgta acagtgttag tgggctattt tatttttttt gctgtggatt    39780 tttttaaaaaa agagtgggg agtagttatg taatggagag gttactctct ccaagaaacg    39840
aatgaaggta aacgaagttt cccgtgtttg gtcataaaac gatgtttaac tttgcacgag    39900
acaggttcaa caaaaacaaa atcttcagtt tcagacttta atttttttcat tgaatgaaac    39960 ttatgtcgct ctgactttgg cataaattcc atcatgccag cgggcgtgcc atcttggtaa    40020
gacagcagaa atttttatatc tttacgtgtg tagccgatta tcagcacttc agtaaagtca    40080
taattaatga ctttaatcca gttcttagac cgttttccga tttcatatac tgagtttgct    40140 tttttttagga cgatgccctc taatccttttt tctttaacca tattgaaata ggagacacca    40200 tttccttta tcccttcaag tacaaaagca ttccggatggt ttatttcaag acctttaagc     40260
acttctttac gttgcgttag tgggtttgat gcgatggatt ggccgtttga ataaatgaca    40320
```

```
tcgaaaatgc aatatacgat cttatgtggg gacttattgg acataaaccg ttccataaca    40380
gcctcaaagt caggagatcc atcggcaccg gttacgatta tttcgccatc taacaccgta    40440
ccgtcaggaa catctaaatt caataactca ggaaacttgc tgctaacttc attgttgtga    40500
cgtgtataaa gctttatatg attattgaat tttgatagta caatccgtat accatcaaat    40560
ttaagctcac tgatataaga atcatcatcg aatggttctt tgtggattc aagcagcata    40620 ggggatataa acaaaaaatc acctccctta tgaaataata aggaaggac gatggcctat    40680 aaagtcattt gaacctggta tataatgcaa actgtttgaa acaagaatca ccggaagctc    40740
gaagaaaatt ggaaacagac aattttttctt ttcagaattt tttacatatg ctatagttgc    40800
tctaaagtta aacattaaag caaataaat ggttcctata actttggca gtatctgagg    40860 ctaattatat gataaggaac aagcccaaat taggggggag tgaccaatag tcactctccc    40920
cttttagtta ctaaatatat tttgtttctt taagacattt aaaacaagaa ttgatgtttt    40980
gttataacat caaactgata aaaataatga agagacatca agtaaaagca taggcggaac    41040
gtcagtttgt taggatttca ttaaaaagca tcatcggaat tgtaacaaaa aaaagtgggg    41100
ataatgttgg ttactacgga aatttgaaag gaggtgattg taatggttga agggctgatt    41160
gttctagcgt tttttttcgct ttggttgatc ttgttaaaaa aatagacctc ccgcaagccg    41220
aaaaatctag agggaagtct accaaaattt aagtttccac tgtccagggt attggtagta    41280
ccctgacagg gaaatccctg acattattat ttccaatatg taagaattta tgctcgatca    41340
aataaggagg tgattgtaat ggttgaaggg ctgattgttc tagcgttttt ttcgctttgg    41400
ttgatcttgt taaaaaaata gacctcccgc aagccgaaaa atctaaaggg aagtctacaa    41460
aaatttaagt tttccactgt ccaaggtgtt ggtagcactt tgggctactt atcatgttat    41520
caaatagagg tattaatgtc atctaacaaa aataaccccg gatggtcatg tccggggccg    41580
gtagaaatca atcctcaagc acaaagattg attatatgta atgatacaca tcgtggtgag    41640
atatgtaaac caggatgtta cttggagtat atcttcattt tttcattggt ctttttgccg    41700
ttcttaatct tatccaggta cttttttaaga aaagaatcat atagactatc cggaatatat    41760
ccaagtcttt gcagcaagag attttcaacg atattcattt tctttgtgag gaattgataa    41820
tcattcctgg attcctgtga atcagtgtta ccggtcgccg ccttcttata aagttcatta    41880
tacttttggc tgcgttttg tctgataagc tttaacaagc aaagcaactc atatgtgtga    41940
aaagtcatta attcaggtgt agtcttgtaa aggtcctctt catcggcagt ttcacggaag    42000
ggaactgttt tgcggctgcc atcttcttcg gcgtcttta tcttgatcat gcagaattca    42060
cattcataat agttagattc gtttctcttt gctacggggc taccgcagta tgggcaagtt    42120
ttcatttcat tgatctcccg tcagttagat ttttaatgtt ctcattaagt gaattcatta    42180
atgagtgatg ttttttcgagg aattctttca tttctttagt cttttatct ttaaatgact    42240 cattggcgga taaagcaaat gaatagtatc ctttaagcaa ttcatttact ttatcaattt    42300
cagcttttaa gtccacaaca tcaggaatct tgcaaaagtt ttctaaggtg gctagtgcat    42360
aacaaataga ttccgaaaac tctaagatta tatctttgtt ctgtttttt aataactcaa    42420 tagggggccca cactttagcc ttgatttctc tatttaacag agagcatttt tcagaactta    42480
tactttcctt ttttactcta ggtctgaagt agttgtattc aacgtatttc agcaatccta    42540 aaaattttttt gtatctagtt atttcaatac tatcacgagg atgtcccaaa actttaaagt    42600
aagatggcgc ctttttgcta tcggtaaatg aaaaagatct acgatacagt tccagttcat    42660
```

```
cttctggatc ttctttatct gtggtatagg caaaacatac aagtctaaag tcaatttctt    42720
gataaatatc tgtgccatac gctcttacat aatattcatt caccttttgcg ttgcggaatt    42780 ctgccccttt tctaaaaaac tcgtaaacaa caccttttt aaagccatac aaacgctcat      42840
aaatatcgtt aagacaaacc actgtataca gatattcaat aggaagttct ttttctaaag    42900
gaagtatagt tttacacatt gttttattca ccttcttat tattccataa tcccaatttc      42960
tttttctttg cttcttttc agcttgtttg tattcatctt catatttaat atttggtgga      43020
aaaacagcta aacgagcata gcccttctct aagagaattt tgttaaatga ggtcccgtcc    43080
tttaaaaata cgtatgccaa tagtctatcg tatttatcac gcttttcttt gtcgtattcc    43140
agataaacac tttgattctc taacgtcttt tttgaaaagg ctgaagcttc ttttccataa    43200
ggctgcactg cttttgttgg atggactgtt tccggagtat cgaccaatat taaacggatt    43260
ctttcctcag taccattaac atcggcaata aatgtgtctc catctataac gcgtctaaca    43320
gttacctcaa ttttatcaga tagatcaacg gtcttttcag ttgttccaga atggctgctg    43380
ctaacgccct ggcatccact aagtaggatg accaggacgg ccaaagcttg cattaacttt    43440
cgagttagca tgttctttct cctttgagcg ttttttttggc tgagaggaat atggctgtaa    43500
ttttaattac agctaaaatt cctgatgtgc ctgccggcag gtattgaata accaggttgt    43560
gctgcggaaa tgtacccgat tctgtgaaga caatttgatt gtcagtttta ttgaatgcca    43620
tagtattata gtctaaatct tcagcaataa aatccgtttc tggtagagtg atagtacggt    43680
tcaagtgagg cgttagatga tcggacacat ccaaatgcca tgacatagct ttcttcatga    43740
ttcattctcc tttttttaag acttttttgg ttttgcttgg ggagccaatc agcattcaca    43800
gtcgaaagga cacaagggt tacgagccgt tgagggtgt tctgtagccc tttacggatc      43860
gttaagacca atttatttgt ggcagctgcg ggcagctgtc cgtttacaaa aaaattggcg    43920
gcccttgtgt gcttttatga aacacggata gtaacgcggc gggcgtgccc ggcgtgttgc    43980
ttgccgatgt tgaatgtgaa atgctaaagc ccccggacag cttcagctgg ccaagtatgg    44040
gggcgtttgg ctgagcaaaa acaaaaaagg cgtctaaaaa aaggatttaa tcatgccggc    44100
ggctgccggc attctttttg cggaaatgcg accggggctt tctgggagcc tttctgcttc    44160
ttttgggttt aagaggctgc tttagcagcc tccaagcagg ctcgatgcct gcgttttaat    44220
caaggaaaac tttagttttc cgaccttgcg taaccggcaa aagccggttg cgattttagc    44280
cgcaacaaat tttgcgccta atttgaactc acgagtttta agtcttttc gtgaactatt      44340 ggaccatctt ccacgtccca gaaagataaa ctttcatcct cacgtaaaag agcttccgta    44400
tctttatagt aaaaatcaac tgctacgtgt gacatctcct catcttcttt gtcatgccaa    44460
ataactttcc ctattgtacc ttttgggaag tgcccccatg gtgaatcgtg atcaactaaa    44520
agctgtactt ttgcacccttt tcgaaatgtt ttcatgtttt ttcctccttt gattttgct      44580 gtccataagt aaatgcgggg ggaccagccc cgcgagtttt tccttgtgct gtgttttttg      44640
attcctacct gtatttaact tgccgtactt atttgatctt cttctgtatt ttctaaaata    44700
tagtcaacag cttttgggc ttgtgcagat gcatggaata tcaggcggtt atcgtctttt      44760
aatgcagaaa gccaggattt gatatagctt gcactattct caatggtatt gttttctatc    44820
ccggcaatgc cgcacagcat agctgcaccc atttctgcca ctagctcttc tttagaatat    44880
ttctcgtcac caaatgtacc aaaggttctt gctaggcgac ttttatggcc tgtactgtgt    44940
atcatttcat ggaaaagagt cgagtagtat tcttctggca ctttaaaatc ttgtattggc    45000
ggacaattga ttttatcgag tgttggaaag tatgcagctt ctccaggttc aaaggtgtag    45060
```

```
gttggaccat tgggatagtt attgataatt tcttcagctt tttcaatggg atcgtgatta    45120
tacgtttctt gttttcgttt acttttttagc ccgtacatt gtttattgat atcccatacg    45180
cggtagtaga taggctttgc aaatttcttt ttttcttctg tttcttcgtc ttcaaactct    45240
ttccataacc agaacacaat gatatgtgag tttttaaatt cttcttttt gatgcggccg     45300 ccagcttcta agatttgttt tttagaagcg tattccccag gagggactaa aaagttattg    45360 atacccgat aaggcttttg tgttttccag ttaactgctg cacaggaatt tgtccagggc     45420
tgatgccaag gaacaacacc cttttcaagt tgtgcaataa ttttctccgt gatgatttca    45480
taaactgatt tccccacaat gtgactctcc tttttttaag acttttttgt ttttgcggag    45540
gccgaattgc attcacagcc aaaaagcaca caaggggtta cgagccgtta aggggtgttc    45600
tgcatccctt tacggatcgt taagaccaat ttatttgtga cagctgcggg cagctgtccg    45660
tttacaaaaa aattggcggc ccttgtgtgc ttttatgaaa cacggatagt aacgcggcgg    45720
gcgtgcccgg cgtgttgctt gccgatgttg aatgtgaaat gctaaagccc ccggacagct    45780
ttagctggcc aaggtggggg cgtttggctg gacaaaaaca aaaaaggcgt ctaaaaaaag   45840
ggtttaatca tgccggcggc tgccggcata cgttttgcgg aaatgcgacc ggtgctttac    45900
gggagccttt ctgcttcttt tgatcttccg tcctcgttca ctcgtgaaga aatggccagg    45960
aacaatgcag ctgttgcttc aggatccgcc gcaggcaatc cggaagctta cagatgtatg    46020
ttatcgggca ttttagaggg aagcgagatg ccgcggaatg ttggccggcg ttttttggccg   46080 gcttacagtc cgggagcaga cccgcagggg gacccaaggg aaattttttaa ccattttttag  46140 aagtagatac gcaacttata gtaactgatg atgtccattt tgaaagaata atacgcagtt    46200
agaattagaa gaggttttca ccataaattt gtgccatttt aaaaatcgct tcgcagttaa    46260
taatgagggt agaaattttc ccttaaatgt gcggtataaa aaaagtgcga gtattatcta    46320
gtgaacatgt aagagagggg tttgaaattt aatgtcccaa aataaatagct taatgcaagt   46380 tatgaagtgt aaaagaaaaa taagactaat cgaaggaagg aggttaaacg gaatggaaaa    46440
aatcagtaag ggagaaagga gaataatat gaataaagag gaactgctgt ggatgttaag     46500
gcttgtctta attacaaatt catttacggc cacaatattg tttggtatgt ttaaagttat    46560
tttgattgct acaggtaatt aaaaagatca gcttaaaaac tgatctaaaa gggtgactga    46620
agatgttcca gcatcagcag tcatcatgat ataaagttgt tgtaattata gcagagaaga    46680 tataagaag aagcttacaa ggttttgatt ggtggtttgc gcagcaaaac caccagagaa     46740
ggttttaatg ttttttagagg ttgctttagc aacctccaag caggctcgat gcctgcgttt   46800
taatcaagga aaactttagt tttccgacct tgcgtaacga gcttaccgcg ctatgtagcg    46860
cggtaacttc ttttttgttat ttgagcagtt cttgttgcgt aattaaccaa ttttcaattt   46920
tttcaactac ttcacaaaaa tcttgatcga atggaaaacc ctcattaagt ttgttaaacg    46980
taacatcatc agattcatcc cataaatcag aaatctcccg tgcggaagtt ttgaatagtg    47040
ttaaggcgtt taataaatttg tttttttgtca ttgcaaaaac tccttgctga accgttcaat  47100
aaagtatgac ggtagtatta taattttttc acttcaacgt ataatgaacc ttccgtgatt   47160
aacgatttaa agctttcgat agcttcttcg gctgcttctt cttctgaatt ggcatctact    47220
tcaatttcgc aaactactag gtactccata ttgttcccct ccgaatttat atagagggac   47280
aggtagacga atcctgtccg atttgtgctt gtgtttttaa tctctaccga gtttctattc   47340
aaatatagcc tttgcggccc tatatgcatt cattgttaat tttctttgcc aggcttgtga   47400
```

```
gtgtggtgac catctaaatg tgtttttctt taatttatct tttaattgat cgtcgggccg    47460
ttgatcatca ggaaagataa tttttaatct gtcgctttct tcatcagcga ctacgcgaca    47520
ctgttcataa gtcaaagtgg gatagtgcgg ctttttttct tcagcttgaa agagtttata    47580
gatgctgtga cgttttgtga aaacttttgt catgccttct gcttcaaata tcttgtataa    47640
ctcttccttg ttgtgtcctt cttttgaatag tcttttttaat ttggtgacga gactgttttt    47700
gaataacgta atatcatatc caggcatttt accttctttt attaggcgga ttcttataca    47760 atctttctg aattcagaat atgcctttac tgctttttct tcgggcttct ctaaggagcc    47820
aagatgtttc tttgtgtttt gaataaaccg tgtcatcttt tcagttgttt ctcgatcata    47880
attgtctttt cgagttaatt ccttttgctt tctttcaaat ggatagtttg cccgtccggt    47940
aatcaaggga cttggtgttt tgatcatggt aagtgatttc tccattcgct gagttaaaaa    48000
tttttcaaac tccatcaacc tatttagaaa ataatctctt tgatcttcat tttgaactag    48060
aggtgctaga tcgttttttaa atttgtttgc ataatactga atttggtgat cgggattgta    48120
tttgtacatg tgcaactcgt tatatctctt tgtgatttca ggttttacgt acgttttttac    48180 tgccattaca tagacactcc ttttttgttt tcatattcaa tcatttttaa tgctcgccaa    48240
aacttaacat caggaattcg taaatcttgc cgtatgtcag acaacagttg caatttgtct    48300
agaactactt tgcattttttc ttggtagagt tgaacttcaa atggacagtt agcaagttct    48360
ttttcttcct ctgttaatt aaggtctagt tctaaatctg taatgtatct ggctaatacc    48420
agcgctattt cttgtttagt cactcatttt cgcccttga ttaaaattg agtggaaggg    48480 gagaccaacc cccaaccgat aaccttgta cgtgtgttct tgatttctac cgttttttatt    48540 ctgtaacttc aaaaaaacgt ttaagtggag gcaaagccca cccatccttt ttggtttggg    48600 caatagctttt tttatacatt gcttcctcaa aagcatcacc taatcgtttt tgctcttttt    48660
ggtaatcacc ttctaaataa acatttaatt gataatcacc aaaatcgatc ttgactatga    48720
tcattttgtc ctccttttttt aagactttt tgttttgcg gaggccgaat tgcattcaca    48780
gctaaaaagc acacaagggt tatgagccgt taagggatgt tctgcagccc tttacggatc    48840
gttaagacca atttatttgt gacagatgcg tgcagctgtc cgttcacaaa aaaattggcg    48900
gcccttgtgt gcttttatga aacacggata gtaacgcggc gggcgtgccc ggcgtgttgc    48960
ttgccgatgt tgaatgtgaa atgctaaagc ccccggacag ctttagctgg ccaaggtggg    49020
ggcgtttggc tggacaaaaa caaaaaaggc gtctaaaaaa agggtttaat catgccggcg    49080
gctgccggca tacgttttgc ggaaatgcga ccggtgcttt acgggagcct ttctgcttct    49140
tttgatcttc cgtcctcgtt cactcgtgaa gaaatggcca ggaacaatgc agctgttgct    49200
tcaggatccg ccgcaggcaa tccggaagct tacagattgc ggaaatgcga ccggtgcttt    49260
acgggagcct ttctgcttct tttgatcttc cgtcctcgtt cactcgtgaa gaaatggcca    49320
ggaacaatgc agctgttgct tcaggatccg ccgcaggcaa tccggaagct tacagatgta    49380
tgttatcggg catttttagag ggaagcgaga tgccgcggaa tgttggccgg cgttttttggc    49440 cggcttacag tccgggagca gacccgcagg gggaccccaa ttaatcttga taacaacgga    49500
tcacaaatgg aaaaaaggat gtgctatgct ttgaaatata aagagggggt ggtgtcaaat    49560
ggatacaaat gaggtactac agttgttaat tgctacgaat ggaactacag caacagtttt    49620
agttgggatg ttcacattaa ttttaacggc acttaaaaag taagatcagt gtattaaaac    49680
acactgatca gcagaatgat tttgtaactg agatgtggct gcatcttcag ttcgctcat    49740 tatagcaaat tgattttggt tttccccctg tttttgcgct agcaaaatca gggggagt    49800
```

```
tttaaaggtt gctttagcaa ccttcaagca ggctcgatgc ctgcttttaa tcaaggaaaa    49860
ctttagtttt cctaccatgc gaaccagcat gattttcatg ctggtttgtt tgccgtaata    49920
tctattaaca ttaacagcaa aattcagatg taacattatc ggtgtaaagc acttcatttt    49980
ctccggcttc ttctggaaaa tacgtttccc catcaaactc gtatcttttc tctgaaagga    50040
cgactgtcat aatagatgaa aagcagtccg ggtcagcgtg gattttatgc atttcctcgt    50100
tagttagttt aaatgatatt cctgcccgtc cccaaattgt tataaagcca ggttcttggg    50160 aggactttt agatgattcc atgttatctc actcctttgg aatggggtgg gtttcctgca    50220
ccgcagatta atacgttaga tgtcgcaatt gcatcctgta gccagccggc agtgtcatcc    50280
atgatgtact cactttgaaa ttcagacagt gagtcatagc cgtgctgttt cgctttactt    50340
tctgcccaat cgctgggaac tgtaaaccag gcacaaccta agtgatcatt tatgccgttc    50400
tcatttggta ttaattcacc aacgtaagtg tagattgtgg tgactttcgc cttttcatag    50460
tttgaaagct ccgcataagg cgggagcgat tgtctttttt tggcttgttt ccacatatat    50520
aatagatcga ttgccgatat ctctgaaagc tttatatagt tcgcttgtgt gttttcgtct    50580
acataaccta agtcgtgaag atcaaagcaa gaatcaagag cttcacaaag ttcttcaaag    50640
gttttgtagc gagtgagaat ttcatagata gttaaagatt tcattgctgt tatcgtctcc    50700
tttggagatt gagggcaggg ggaccaatcc ctgccaacca atctgtatgc ttgtgttttt    50760
aatttctacc gttttcaca tttactcgtt cataatcgaa atcgttgctg tttggaacta    50820
atttttcgcc taaatgctcg cattctataa ccttccactt tagcggagaa accagtctt    50880 gtaggtatcc catagcgttt gcttcggtgt caggaacagg cataggaatg actattgccg    50940
gatcgccttg ttgttttttca agagttgctt gatatatgtc aaaatgcact tggtttatca    51000
ttttgataac acccctgtat ttgagatttc aaactgtttt ctatggcagt aagacacgtt    51060
tggaaagtaa actcattctc tatatcttta taggtgaaaa catagcctat acggaaaaaa    51120
tgatacttac cgttgcgttt aaaaatagat tctacgaaac aatcaaattc atttatccct    51180
tgttcgtcag aatcgcaata catagcaggc tcatatgata tgaactcatt ctctgaaaag    51240
aattgattat gatccatgaa attcaaaatt actgtatcta tgaagtcgca gaaagtgccg    51300
caaatagctt ccaaactttc ttctgaatga cttttgtaaca aggctttatc gaaaggtata    51360
gcttcaggta tgcctgttaa tgcttggtac tcttcttttgg ctatttcaag aaactcattg    51420
agtgacatag aaccaactag attcacgtct gctgtattga cattcatttg accctctcct    51480
tttgagtttt taggaaaatt tactgcaaca aactacacca agaaacgcta tggcaattag    51540
taaaaccaag atggaatacc ttttgccttc accttttgtt ctgatagtga taactgataa    51600
aaagccaaat aatgaaagtg ctattatcac taaaatgatc tcttgcatgt gaattctcct    51660 tttttaaga cttttttgtt tttgcggagg ccgaattgca ttcacagcca aaaagcacac    51720
aaggggttac gatccgttaa ggggtgttct gtggcccttt acggatcgtt aagaccaatt    51780
tatttgtgac agctgcgggc agctgtccgt ttacaaaaaa attggcggcc cttgtgtgct    51840
tttatgaaac acggatagta acgcggcggg cgtgcccggc gtgttgcttg ccgatgttga    51900
atgtgaaatg ctaaagcccc cgggcagctt tagctggcca agaatggggg cgtttggctg    51960
gacaaaaaca aaaaggcgt ctaaaaaaag atttaatcat gccggcagct gccggcattc    52020
tttttgcgga aatgcgaccg gggctttacg ggagcctttc tgctttttt gatcttccgt    52080 cctcgttcac tcgtgaagaa atgaccagga acaatgcagc tgttgcttca ggatccgccg    52140
```

```
caggcaatcc ggaagcttac agatgcatgt tatcgggcat tttagaggga agcgagatgc    52200
cgcggaatgt tggccggcgt ttttggccgg cttacagtcc gggagcagac ccgtaggggg    52260
accccaaagt aaggattcct gaaaaatcct aaagaaatct aatgtaatcg atatgagata    52320
tagctctttc agctggactc tgaagggtta ggggtgttga aagggg tttg taaggctttg   52380 tgttaacaaa gccttacaag aggttttt gt ggttttagag gctgctttag cagcctccaa   52440
gcaggctcga tgcctgcttt tgatcaagga aaactttagt tttccgtcca ttcgtccgcc    52500
aaaggcggcg aaaaaaccag gctatttgaa gcctgatttt acaatgttat tttgaccata    52560
tttgtctgtt tcggctgtaa ggggctgtat cgtcaaaatg aagtgtttct tttagtctaa    52620 accctaatttt ttcaacgtat ctaaggcgtt tcttcatccc aaaaggataa tcgactttga   52680
tttcactagc tgcttccagg tgtgctggga ggtctttgta acgactgctt atgattcttc    52740
cggaatctgc tgtaattggt ttatagatag ttactgaatt atcgagtctt acaagtatca    52800
tcatgtatcg ctcctttgga atggggatgc ttaagctatg aggttcccga agattactgt    52860
tccgaaaaac aacagtccga ttaaagaaag tgatattcgt ggactgactg ctataatttt    52920
gtcatcgaat acgatgatct ctccctggga ttcaagttca gcaatatgag tcatgacctt    52980
atttgaatcg ccatattta atagtttgct gattgtggta tactttgatt cacgtattga    53040
tttgagcagt gattctttgg tcggggtcac atgctctttt tttatttt cc gttgaattgc   53100 ttgtgctgca ttcatattca ttctccttca tcctccttca aaatagttag cccactttca    53160 ctttt atttt ccgttgctat ttcaaaaatg agtttagttt ggtcgtacgt atattcactc    53220
gtgaaggtac tgatatcagg gatatcagtg aatctgcggt ttagaacttc ttctaaccag    53280
tcctcgtaaa cacaaaatct tacctgtgtt tcagggtatt cattggcgga cgctttataa    53340
gtccaaaaac tgcagtacgc ctttgactgg gttttatcta gctgtgattc gattgatcca    53400
attaggtcat ctaatattgt ccatccttct tcaacgcttc tttcttttaa tgtttgttca    53460
aagccattgg taatgcaggc ttcaatattc ttctcagtgc caaggaatcc tttggattct    53520
aatgcggatt tcaggtcttc tttatgccat acaatagatg tgaaaaacat atgtaacagc    53580
tccttttttt ttaagacttt tttgtttttg cggaggccga attgcattca cagccaaaaa    53640
gcacacaagg ggttacgatc cgttaagggg tgttctgcag ccctttacgg atcgttaaga    53700
ccaatttatt tgtgacagat gcgtgcagct gtccgttcac aaaaaaattg gcggcccttg    53760 tgtgcttttta tgaaacacgg atagtaacgc ggcgggcgtg cccggcgtgt tgcttgccga    53820
tgttgaatgt gaaatgctaa agcccccgga cagcttt agc tggccaaggt gggggcgttt    53880
ggctggacaa aaacaaaaaa ggcgtctaaa aaaaagattt aatcatgccg gcgcctgccg    53940
gcaatcgttt tgcggaaatg cgaccggagt tacgggagcc tttctgcttc ttttgaacct    54000
ctgtcctcgt tcactcgtta agaaatggcc aggaacaatg cagctgttgc ttcgggatcc    54060
gccgcaggca atccggaagc ttacagatgc atgttatcgg gcattttaga gggaagcgag    54120
atgccgcgga atgttggccg gcgttttggg ccggcttaca gtccgggagc agacccggag    54180 gggacccca a agtaaggatt ctaaaaaact cctgaaagaa atgattaaat gtaatcgata    54240
tgaggtgtaa tgtgaaaatc aatctttctg ctgagctgtg aaggtgttag gggcgttgaa    54300
agtgtttgta aggctttgtg ttaacaaagc cttacaagaa gatttttgtg gtttttaagg    54360
ctgctttagc agcctccaag caggctcgat gcctgctttt aatcaaggaa aacattagtt    54420
ttccgtccat ccgagaactt caatggattg ctcatagtcg atgacgccgg ctgtcctcga    54480
agcaatcagg gtacttattc tgttttctttt ctaaaaagga tttaactttt attgctatat    54540
```

```
agtcaaatag tagatcaagt gctttgttga ttaaccattc aattaataag acactaagaa    54600
tatatttcat ataaaatgtt cctccttacc cgtgatatat ataaatatca attttttcaat   54660 acaaagactt ttatggaatt caaagaaata tttcaaagaa atttgatagc agaattatca    54720
aaatttgggt aagattgaat tgttgagttt catttaagtg tgtgaagaaa aatgctgaag    54780
atatgctaaa aattaccgat agaaagtata ggattggaaa gagaggtagg catgaagaat    54840
ataaagcata ttaaaaagat gaggaacagt atactattct cagttgtatg gcgtttgttg    54900
tttttagtat tatatccagt aattttaggt gctggactgc cattgattgg gcttaattta    54960
ccttcagcaa cgctgtttat attaagtttt attggttgta tgatggtctg tttaactata    55020
gctactcata taagtaatct ggttaacata agagaagttc taaaacagta tgcttcaatt    55080
gagagagaac ttgttggaac atattcaatt gatgcaaagg ttttggacga catgcttgat    55140
aatacaatga aaaagtatca tcatcaaaga tcattcgacc gagactataa cttagcggat    55200
ttgcatgcta ttgaagagtt agttcaggaa gaaagaaatg gtaagtattt tgataaatac    55260
ctggctcatg atgacagtat caaggatgaa attcgaatgg ccgttgtacc gaaacgggta    55320
gctgaggatc tcttatattc agttttcaac tcaaaaacca catttggaat aaccggaaga    55380
aaatactatc ataaatggca tatggctcga ttagatgaac agctgctacc gttcttacaa    55440
gaaaaacaag aaaaaatgca taaaacaaat tagattaaag tacctgaagc ttttcaggtg    55500 ctttttttgtt taggaaaaac tttcttgtac taaaggaacg tatgttctgt taatatataa    55560
tcaaaaatgt ttgagggtgt gatcaagtga taaaggatcg aggtttaatg aaatgggcaa    55620
cttctatgat gttgccggag cacaacgaaa tgttaaagca gctgaatctt gaaatggaaa    55680
aaatgaagcg ccctgaaaat gatgaacaaa aaattgaagc aatggcccct ataattaatg    55740
aagcaaaaca aggaaaccaa cttttaagta tctcctattt tgaaaatggc catatttcat    55800
cgcttacagg ctttgtaagg tcttttaagt acattgagag ggaaatgtta ataaaaacga    55860
atgaagggca tattaaggct gtttcagttg atgatttgat cgaggtggag ctggctgaag    55920
gagaaaagtt ttatgattga ctatgatagc cttcctaaac gtacttttt gaccgtagat     55980 atgcgtagct tttacgccag tgcatctgca gttatgctgg gcctcgatcc catgaaatgt    56040
tatctcgctg tggtaggcga tactgaacga tcaggaagtg ttgttttagc tgcatcaccg    56100
gctttaaaaa aacgatttgg tattaaaaca ggttcgcgcc tttatgaaat acctgatcat    56160
cctcaaattc acattgtaaa tcctcagatg cggatgttta ttaagctttc caccaatata    56220
actcatttgt tttatcagtt tgcttcacct gaagatatac tcacctatag tgtcgactct    56280
aggggcctgc accctaggga taacagggta atattgtgca gggcccctag aggatcattt    56340
tttaatgtgg tcttttattc ttcaactaaa gcacccatta gttcaacaaa cgaaaattgg    56400
ataaagtggg atatttttaa aatatatatt tatgttacag taatattgac ttttaaaaaa    56460
ggattgattc taatgaagaa agcagacaag taagcctcct aaattcactt tagataaaaa    56520
tttaggaggc atatcaaatg aactttaata aaattgattt agacaattgg aagagaaaag    56580
agatatttaa tcattatttg aaccaacaaa cgacttttag tataaccaca gaaattgata    56640
ttagtgtttt ataccgaaac ataaaacaag aaggatataa attttaccct gcatttattt    56700
tcttagtgac aagggtgata aactcaaata cagctttag aactggttac aatagcgacg    56760
gagagttagg ttattgggat aagttagagc cactttatac aatttttgat ggtgtatcta    56820
aaacattctc tggtatttgg actcctgtaa agaatgactt caaagagttt tatgatttat    56880
```

```
accttctga tgtagagaaa tataatggtt cggggaaatt gtttcccaaa acacctatac   56940
ctgaaaatgc ttttctctt tctattattc catggacttc atttactggg tttaacttaa   57000
atatcaataa taatagtaat taccttctac ccattattac agcaggaaaa ttcattaata   57060
aaggtaattc aatatattta ccgctatctt tacaggtaca tcattctgtt tgtgatggtt   57120
atcatgcagg attgtttatg aactctattc aggaattgtc agataggcct aatgactggc   57180
ttttataata tgagataatg ccgactgtac tttttacagt cggttttcta atgtcactaa   57240
cctgccccgt tagttgaaga aggttttat attacagctc cagatctaga gtcgacgaga   57300
gtataattag atttgatttt ttgaagagac tatggggaac accgatggat ctggcgaaaa   57360
gaatacaaaa tgcaatctac agagattttg gtgtaccagc aacagtagga atcggcccaa   57420
atatgctaat gtcaaaacta gccttagact tagaagccaa gaaaagccct tcaggaattg   57480
cggaatggac atatgaagac gttcaaacaa aattatggcc agttcatcca ttatcgaaaa   57540 tgtgggggcat aggaaggcga atggagagga atctgaatcg aatgggaatc gccacagtag   57600
gacagcttgc aaattatccc ttagaactat tagaaaatcg atttggcatc atggggaatc   57660 agattttatta tcatgcccat ggtgtggatc ttagcgagct gggaacgcct attaggcaag   57720
aacaaatttc tttcgggaaa agccagatat tgttgaggga ctacaatgaa gaagctgaaa   57780
ttaaatcagt catattagaa atgtgtgaag aagtggccag ccgggctaga aaggctaaaa   57840
aggcaggcag aaccattcat ttaggagtag gttatagtca aacagtaggc ggaggcggct   57900
ttcatcggtc tttaacaata gaccaaccaa cgaatatcac gatgaaactt tataaagcgt   57960
gcattgcttt atttaagaaa ttctatcaag gtcaaacggt aaggagctta tcagttacat   58020
tagggaacgt agttgatgat aaccaatttc agatgtctct ttttgaagaa aacagtgaaa   58080
aggaacgtca acttggccat gttatggatt ctattaggga aaaatacgga tcagatgcga   58140
ttttaagagc tatttcttat acaacagctg gaactgcatt aaaacgggca agcttgtgg   58200 gtggccatca agcataaaag tacatgaaga tagtgaatgt cactattaat atttcaaatt   58260
cattaaacaa aaagagcctg aagtaagtat caggctcttt tttaaaaaaa cacaaaaaac   58320
aagatttcta cttgaaatct tttaaaaatt gtgatataat actatgtaag taggcgtatg   58380 ccttttggt tcagcttttc tgtttgatga tacgggaata tcatcttcag tatctgatgt   58440
gttgattgtt agtcaacaac gttacattga ctataatatc tcacaagttt accgttgtca   58500
actaggtttt tgtaaaaaag tgttttgaca atagcataca tactgattat gcagatttga   58560
tggtttcaaa aagtgcatat tgcctgctta aaataaattt aaggaggtaa tgcacagtgt   58620
gtaaattaac gttgcattac agaagaccac ataaggttag aggacatttt agaaattgta   58680
agggaggccg tgtttggatt cctgaacacg aaaggggtgg aacttgggtg aatgaccatt   58740
gctacccagg tttcttgcct gaacttccaa gttaatactg aaggtcctca gtggcctttc   58800 tgattattc ctcgctgttt tggcagctta gtagctgccc cctttttaa gagatatctc   58860 tttagttagc aacatttaaa acttctatag gatttcaatt gctagacatg atatactcgt   58920
taggaagata tttactggaa acaagggagg cgggaaaatg aaaaagaaat tcattggatt   58980
cttggtctta gcttcttttt tgttgatgtt taatacggct tcatatgcaa gtggaactga   59040
cgaaaacaca gagaaatcaa ctgctgaatt gttggaaagt gtaatggatg atttttggatt   59100 attcagtttt caaattggcc gaacagatcc gacgattaca attgggatgg atcaaaccaa   59160
aagtgaatca aaacttcgtg aatacttaga tgataatttg tctgaagaag caagaaaaa   59220 gtatgaaatc tatatatttta aagaggatat tgataagttg aaacaagaac atcaaaagag   59280
```

```
tttacaggaa taaagcagac cgactaaggt ctgcttttt  atatcaaaat tagttatacc   59340
acaaagtagc ttgatttatt gtaattaatt tatcagtgtt tccttcattt tcgaatttaa   59400
tgtgatagct tttccctttt tttaagttcc aattcatatg aaattggcct ttccatccac   59460
caggtaaagt aaccttttgg gcacgacctt tagccccacc tctaccatca tcgtaaaatg   59520
cggatacaga aaactttctc gctgttcctt tataggttac gatgagggta cttggatctt   59580
taaaagttt  tccatatgtc cctttccaa  gccaaatgtt atagtaaaaa tcaaagtagc   59640
ctgatgaata tgttttttc  aataccttta ttggattatc tgtaggctgc tcttctgtaa   59700
gtctaatcat gcttttcagc tgttcagttg tataaggatg aatctctttg ttattttcgt   59760
caaaatttt  gatttgagaa gcaatctctt ccttcttagc ttcaatttca tcctgtgaca   59820
gaatttttc  ctcaataggc aaagattctt ttacctctgc tgcctctact ttgcttgttc   59880
ccatgaaatc aaaaagagaa ataccccaaaa cagctgctat tgaccagtac ttgaagtttg   59940
ctttcatatt gaacggctcc tttattcatt ttttaatttg ctaaagttgc attgaatttt   60000
cttatgtttt ctcactggtg aaatttttac tgaggaatcc tatggagtat agatacagct   60060
gataatttga gccattaaag ctgtggaagc tattcatggg gttttgggtt ctttcgtaat   60120
gactcaatca gcaaaagaga aaaattaaac gataatgtga aatctaaatt agtgttgacg   60180
ttggcagcca gtaattttta tcaagacaaa ttaaccccctc ctttgaatga taatacaaag   60240
caaaactacc atagagatca ggaatattac aacaaaaaac accaaaataa ttgaaaatta   60300
tctatatttc tacaattatg tacataatta tatgctttat gtacatatat tctctgaaca   60360
gtgaaaccag ctgcagctga agaaaagatg ttgccggtac cggaaaccag gaagccaggt   60420
gcgacttgtc gtgatgtggc agctgaagaa agagatcgat gccaggcatc caggagcgaa   60480
ccagctgcag ctgaagaaaa gatgctgccg gtaccggaaa ccaggaagcc aggcgcggct   60540
gtgtcggtga tgcgcgcagc tgaagaagat caatgtctgg aattgtgaga cagaactatt   60600
tggtcataaa aaagaaccag tggcttcctg gttctcattg atttatggcc ataattggct   60660
cttatatatg tttacgtact ttttgttttcc tagacgtctt gttagtgctg tccacttcaa   60720
atagctcctg tctaaccatt ggataaacga atttataaaa taggtatcca agtgcagagc   60780
ctagggtgtt taatataaga tcatctacat caaagcttct gtatgtgagt ccaatcgctg   60840
atgatatagt aaactgtgag gtttctatga tgagtgaagc aataaaccca gcgataataa   60900
cacgctttgc ttgtctcatt ctgttgaaaa gaagaggaag aaaacatcct aatgggaaca   60960
agagtattat atttccgccg agctgatata cggttacgga taaacttgag cctgttagtg   61020
catccttcat ggtgttaaaa ggtatgaggt tattagtttc ttggaagcct tctgcggctc   61080
tgtcatgaat taataaaggg tcagttggaa ttggaaatag cgtcatacaa ataacgcctg   61140
taagataaac aaaagtagca agtatataaa tactttttctc tattgtatat ctcggcttct   61200
tttgcacaaa aacagcaaat aaacgataaa caacaaacaa aacataagcg taaacaacgt   61260
acggaataat aaaaactatta agtaacacta tatcacccta ttcttataat aagctgttac   61320
ttaattgtaa atgtccccgt atcctcctgt cgatgctcca ttattcttct ttttcataat   61380
aaaataaaat ttcccttttag ttttatttcc ataactgttt gtagttgaac cgttttgaga   61440
gaacttttta gagccaagat atttggcttt gcctttttc  tgttttctgt atagttcaat   61500
gttaaaagtg ccaccactac cacctgtgtc agcatgagta taaattttaa tattactagc   61560
accgcggctg tacgttttag aagtaacttg atgtttaaac tcaaaccaaa aatcatgctt   61620
```

```
tgatgcagcc aatgcagctg gtgccgttac agggagtagt aatgtaaaac ttagagctga   61680
agagactaga acttttttaa ttttttttcaa gaaaaaaacc tcctttaata tggtaatcca   61740
aaacaaaatt accatagggaa ttaagcggtt acaacaaaaa atatcaaaat aattgaatat   61800
tcactaattc tctacatttt atgtgcataa ttacatattt tatgtacata tgagatgata   61860
taagtgtcac cggcttaatc ttttggagaa gtagcatgca gtcaccatgc ctacaatttt   61920
aattggttgt acatatttta aagagttaca gaataacata gtaacagatg aaaactgtta   61980
cgctgttaca gtgttagtgg gataatctca ataagttga tgtttagttg ggggagaag    62040 atgatatgaa gaaaaaaacg actaaccagg tcgaagaaag aaaagtacgt tcggataaaa   62100
aaacacgagt taatccttca ttggatgcaa atacacatga aaagctgaag aagttggcca   62160
tttcttgtga tatgacaaag acacagttag cagctgaaat tcttaagatg gcgctcaaca   62220
atgagagtgt aattgactgg tatcaaaaaa aatacaacaa agacgattca tatagaatta   62280
tccttgcccg tattaatggt gaattgcatt attcttaacc aactttcccc caggtgcggc   62340
caattttttt ccagagttta aaacaactag aacaaagttt ttgattctta ttatattttt   62400
cttttgacat ccggaccgtt ttaccacaat gtttacattt cattttatg acctcccttt    62460 aatagtatca gcattgccaa taaaacagat tttatacaga ttaagtggat tctaatgttg   62520
ctcagggcgt ctgtgttgca actaaaaaaa gtttgtcatg caatcctccc ttaaatggca   62580 taaaaaaga gcctagatta tccaggctc ttaaaaatca tagtcgtatt cttcttcaat    62640
agttccagtg attttttcag tgattaactg accttcttca atcgtttctg aagctgactt   62700
tggatcagct gttttgtgtt ctacgtagat cgatccctga tcaatttttct tcctcaaatc   62760 acgaaattct ttcttcattt cttctctcat ggcaattaat tcatcatgaa catgacgatc   62820
tttttctcta ttctgctgtt cctctttctg ttgttgcatg tcccttttcta tgagctgaaa   62880 ggcatactct ctaaaggtac ccttactctt acctttactg aatgtactaa tctgctctaa   62940
aacaaaatcg tacatttcat cagacatttg tgttgttcgg acattaaaga gtggaattct   63000 tttgttttc cccatttcta atcacctaaa ttgattgtgc ctcttttca tttgcctgtt    63060 tctttacttg ttcagcgcgg cttaaaactt caaggccata taagttgagc agtcttgcat   63120
cctcagcaac tatatgattt gattcagaaa tatcacggcc atatctctct tcagtaacca   63180
cactaattga ttcttcaagc acctcgccaa caccgccaaa ataaaggtat ttgtaaacct   63240 tatctttttgg tgcagggaac gtattttcag cttgggctat tttgatttct gtgtattctt   63300
taagagattt tttgatgata tcagttaaat caaatttctg accggtattc ccgtctcttc   63360
gttccatctt agttttttcca atatttgagt atataaactt ttcaagctcc ctaacgctat   63420
caaagtgctc taggagtttt tcttttctca attttttctaa gtgcgctaaa aacggtgctt   63480
cggtattaga aacaaaagaa tcacgacttt ttggcggttt taatccagct ggtagtaata   63540
ctagatcatc tgttccgcca cctaaatcac aaaaaactac gtcataattt ttaaattgtt   63600
cggcatagtc tttatcttct aggtcaaagt ttttctttat tgcccatctt gctacttcag   63660
attcgatcct gcacgctgca tcttccactt ttatagtaag ctcttttttct aatcctaatg   63720 tcagcacctt tacttggtga gtgcccaaaa atttagatgc catccttttc tgcatttcac   63780
tgaacttatc caattttttta agaagccaaa ttggtagcat tgtttgaaag tattcaatag   63840
taacttcatt atcttcacgt ttgccttta gcgcttggta ataagcagtt gcagctaaaa   63900
atgttacgta tggaatatgt gactctactt tattatgtaa cttcttgatg tgttggttgc   63960
ctaacacttc tggttcagca agttcaccaa ctagaaaata tctctctgtt tcatcaataa   64020
```

```
ctgtagaaac taataaccgg tcctttaaat ctgccggatc ttcaacgata ctcgtaaatt    64080
ttccttcagc agcttcttta gatatctcta ctacatttgt aggcaattca aaaaaataac    64140
catcaattaa attcatgtac atactgtttc caaagtccac gttcatacga gaaatattca    64200 tattttatt ctctcctttg atttcacttt cctcaatact agcatcttat atcactaaag    64260
tcaataaaat gaaatcacat ttaaaatcag tgaatacagg ctatttgagg attatataat    64320
aaaaatgaaa tcagtgaaat cagtagagaa aagtgatttc aggcccgggg ctttacgtca    64380
aaaaaaaaat cgtgtaagat aaagtcaagt taagtcaatg tgaaagtttt ggcattgaat    64440
tctggttcta gttattctaa ataaacaaca aaaaaccctg ttgtttgcag acaacaaggt    64500
taatagattt gatgatacat attttgtttg cgagctattt gcaaaattga atacaaataa    64560
agaatgacaa ataaaaagtg tccgatgttg cagcatcgaa cacttggttt gtaagccctc    64620
acttacaatg tttaagttat gtcttcattt taccgaaaac aagtgtatac gtcaacactt    64680
ttcggctatt tttggacgac agaaaaccac tgtttggagg gtatcaaacc gtggttttct    64740
gtcgtttttt gtttgtcacc cagctgccgt taagggtgt aaaataaact gacgtcagga    64800
gttgccccgt ccaccgcaaa cccggggata taccacaata agcgttcctt gctgcgcttg    64860
tggtgaatgg cgaggacggc cattaacggt ccggagaatg tggataaacc actaggttgc    64920
ttggcgcact acggtgcggg caactatggc caagcttcta tgcagcggca cacaattgag    64980
tgtgaccgtg tgagagaaca cgagacaaac cccatagaag ttgcatacag gacaagcatt    65040
gtatgtaaaa aggtcatggc aggcgaaagc ctggcgatag caaggcagag ctggaaacct    65100
cagacgtctc tatgacgcta gtttcaaatc ctgatcgatt gcctatgtct gtccgttttt    65160 atttttgcg cgacagacat aggcaatcga aattcgccct gtttcctaga acagtcagct    65220
attctgctag tttcaagttc tcaaagtcaa gagaaaaaca ctaaataaat gcgaatttcc    65280
ttaaacccca gaggttttaa gttccttttt aagggttgtt cgtttgatag aacattagta    65340
ttttaatata tttttcctgt gggatttcac taacgtatac tgttattccc tttggcctat    65400
cttaaaaact tgtatagatt gtgtttgagc cgtttagtat gatatcagta catgcttggg    65460
ttcagagcat caaaatgaga tttgaacatt aagcactatg tactaaatgt tc             65512
```

TRANSFORMATION METHOD OF GRAM-POSITIVE BACTERIA

Reference to Sequence Listing Submitted Via EFS-WEB

This application includes an electronically submitted sequence listing in .txt format. The .txt file contains a sequence listing entitled "2020-06-05 SequenceListing 0283-0478PUS1.txt" created on Jun. 5, 2020, and is 91.865 bytes in size. The sequence listing contained in this .txt file is part of the specification, does not contain new matter, and is hereby incorporated by reference herein in its entirety.

TECHNICAL FIELD

The present invention relates to a transformation method for gram-positive bacteria.

BACKGROUND ART

Conventionally known transformation methods for bacteria and the like include a competent cell transformation method in which a recombinant plasmid or a DNA fragment is introduced into a host such as E.coli (see Non Patent Document 1), a protoplast transformation method, an electroporation method, an agrobacterium method, a particle gun method, a calcium phosphate method, and a lipofection method. However, it is difficult for such conventional transformation methods to introduce a DNA fragment having a large size of, for example, 100 kb or more into a host DNA.

Known methods for introducing a DNA fragment having a large size into a host DNA include a method employing conjugational transfer using *Bacillus subtilis* having acquired natural transformation ability. This method has, however, disadvantages that special culture conditions for leading *Bacillus subtilis* to cells having high natural transformation ability are necessary, and that the transformation itself takes time and effort. Besides, it is difficult to introduce a DNA having a large size exceeding several hundred kb intact into a host DNA.

On the other hand, it is known that plasmid pLS20 derived from *Bacillus natto* has ability of replicative transfer from gram-positive bacteria cells of *Bacillus subtilis* or the like to other gram-positive bacteria cells by conjugational transfer. Besides, it has been revealed that pLS20 functions as a helper plasmid in a donor and can transfer a donor's plasmid to a recipient (see Non Patent Documents 2 and 3). Since pLS20 working as the helper plasmid is also transferred to the other gram-positive bacteria of the recipient side simultaneously with the pLS20 plasmid, it can further repeat the conjugational transfer into other gram-positive bacteria as the donor, which can be a problem from the viewpoint of control of the natural environment (see Non Patent Documents 4 and 5).

PRIOR ART DOCUMENTS

Non Patent Document

Non Patent Document 1: J. Bacterial. 93, 1967; 1925
Non Patent Document 2: Ramsay JP, Firth N. Curr Opin Microbiol. 2017; 38: 1-9
Non Patent Document 3: Tanaka T, Kuroda M, Sakaguchi K. J Bacteriol. 1977; 129: 1487-94
Non Patent Document 4: Davies J. Davies D., Microbiol Mol Biol Rev. 2010; 74: 417-33
Non Patent Document 5: Berglund, B., Infect Ecol Epidemiol. 2015; 5: 28564

SUMMARY OF INVENTION

Technical Problem

Under these circumstances, an object of the present invention is to provide a simple and efficient novel transformation method for gram-positive bacteria by which a DNA having a large size can be introduced intact into a host DNA of gram-positive bacteria. Another object is to provide a method in which an artificially designed long DNA can be produced by accumulating a desired DNA segment in a chromosome of a recipient (recipient bacteria), and a method in which transformed cells do not cause a problem also from the viewpoint of control of the natural environment.

Solution to Problem

As a result of earnest studies made for solving the above-described problem, the present inventors found the following: When pLS20catAoriT obtained by inactivation of an $oriT_{LS20}$ region in pLS20cat is used as a helper plasmid, the helper plasmid itself is not transferred to a recipient (recipient bacteria) side in conjugational transfer of gram-positive bacteria but transformed cells to which a desired chromosome or plasmid alone has been transferred can be produced. According to the method of the present invention, the obtained transformed cells do not contain the helper plasmid, and hence can be subjected to, as a recipient (recipient bacteria), the conjugational transfer of the desired chromosome or plasmid again in the same manner. Accordingly, a long DNA can be designed and produced by accumulating a desired DNA segment in a chromosome of a recipient (recipient bacteria) by the present invention. Besides, since the transformed cells obtained by the method of the present invention do not contain the helper plasmid, and hence do not further repeat the conjugational transfer as the donor, a problem from the viewpoint of control of the natural environment does not occur. Furthermore, transformation performed by the method of the present invention can be rapidly and simply performed merely by mixing culture fluids of a donor (donor bacteria) and a recipient (recipient bacteria), and hence can be suitably employed for producing microorganisms, cultured cells or the like in synthetic biological industrial activities. Specifically, the summary of the present invention is as follows:

[1] A transformation method for gram-positive bacteria by conjugational transfer, comprising using a helper plasmid having an inactivated origin of DNA transfer (oriT) region.

[2] The transformation method according to [1], wherein the helper plasmid is a plasmid derived from pLS20cat by inactivation of an origin of DNA transfer (oriT) region therein.

[3] The transformation method according to [1] or [2], wherein donor bacteria in the conjugational transfer contain the helper plasmid having an inactivated origin of DNA transfer (oriT) region, and a chromosomal DNA or plasmid having the origin of DNA transfer (oriT) region integrated therein.

[4] The transformation method according to [3], wherein the donor bacteria are at least one type of bacteria selected from the group consisting of gram-positive bacteria.

[5] The transformation method according to [3] or [4], wherein a recipient bacteria used in the conjugational transfer is at least one type of bacteria selected from the group consisting of gram positive bacteria.

[6] The transformation method according to [5], wherein the donor bacteria and the recipient bacteria are *Bacillus subtilis*.

[7] A transformation method for gram-positive bacteria, comprising the steps of: (1) preparing donor bacteria containing a helper plasmid having an inactivated origin of DNA transfer (oriT) region, and a chromosomal DNA or plasmid having an origin of DNA transfer (oriT) region; and (2) performing conjugational transfer from the donor bacteria to recipient bacteria.

[8] The transformation method according to [7], comprising accumulating a desired DNA segment in a chromosome of the recipient bacteria by repeatedly performing the steps (1) and (2) using transformed cells obtained by the conjugational transfer as recipient bacteria.

[9] Gram-positive bacteria containing a helper plasmid having an inactivated origin of DNA transfer (oriT) region, and a chromosomal DNA or plasmid having the origin of DNA transfer (oriT) region.

[10] A helper plasmid having an inactivated origin of DNA transfer (oriT) region, for use in transformation of gram-positive bacteria by conjugational transfer.

Advantageous Effects of Invention

According to a transformation method for gram-positive bacteria of the present invention, a large size DNA can be transferred to a recipient side intact and in a short period of time. Besides, since pLS20catΔoriT obtained by inactivation of an oriT$_{LS20}$ region in pLS20cat is used as a helper plasmid, the helper plasmid itself is not transferred to the recipient side in conjugational transfer of gram-positive bacteria but transformed cells to which a desired chromosome or plasmid alone has been transferred can be produced. According to the method of the present invention, the obtained transformed cells do not contain the helper plasmid, and hence can be subjected to, as a recipient (recipient bacteria), the conjugational transfer of the desired chromosome or plasmid again in the same manner. Accordingly, a long DNA can be designed and produced by accumulating a desired DNA segment in a chromosome of a recipient (recipient bacteria) by the present invention. Besides, since the transformed cells obtained by the method of the present invention do not contain the helper plasmid, and hence do not further repeat the conjugational transfer as the donor, a problem from the viewpoint of control of the natural environment does not occur. Furthermore, transformation performed by the method of the present invention can be rapidly and simply performed merely by mixing culture fluids of a donor (donor bacteria) and a recipient (recipient bacteria), and hence can be suitably employed for producing microorganisms, cultured cells or the like in synthetic biological industrial activities.

DESCRIPTION OF EMBODIMENTS

Figure 1:
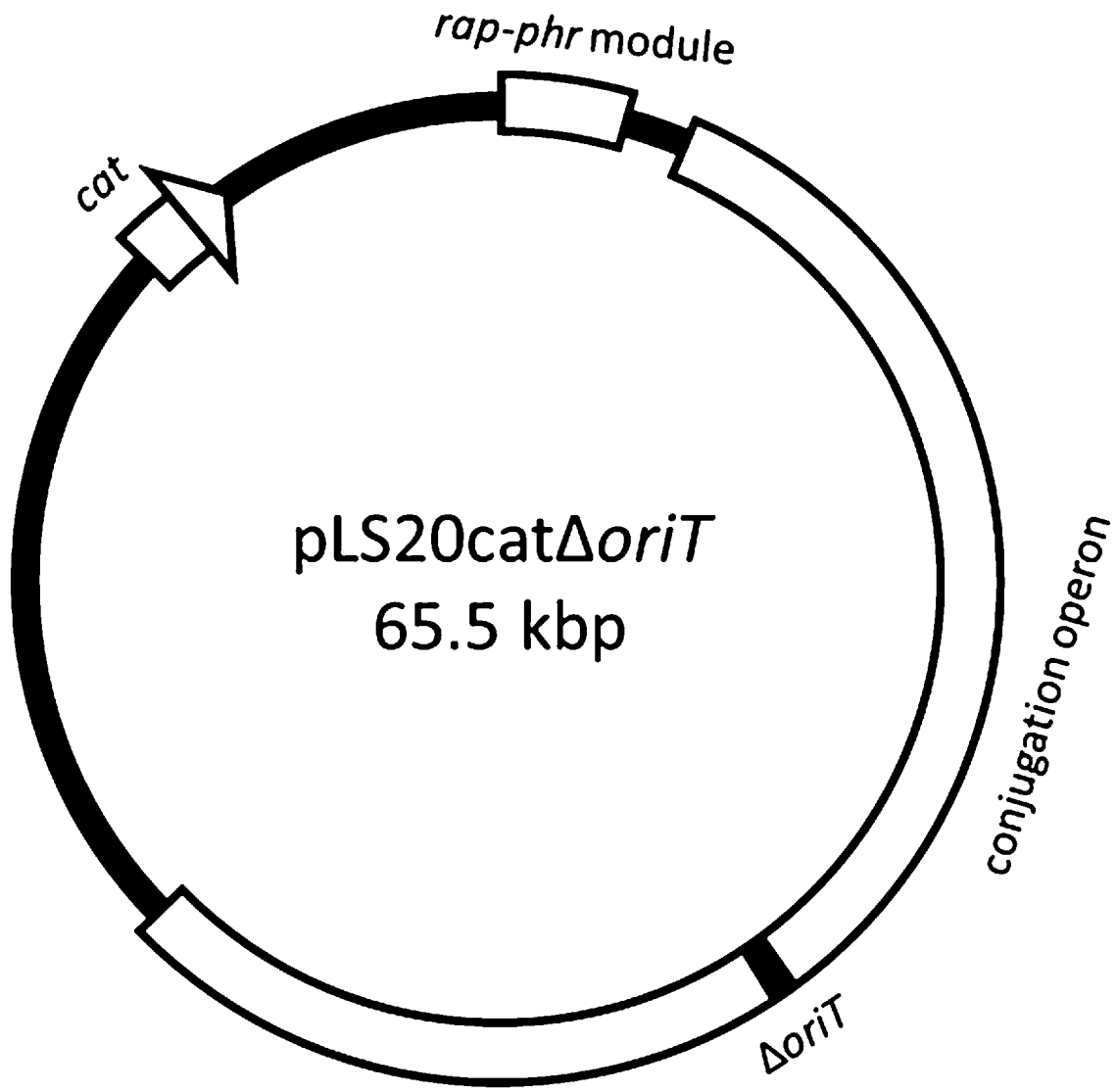
FIG. 1 is a diagram schematically illustrating a structure of a plasmid pLS20catΔoriT.

Now, a transformation method for gram-positive bacteria of the present invention will be described in detail. It is noted that molecular biological methods employed herein for preparing a DNA and a vector can be performed by methods described in general experiment books known to those skilled in the art or equivalent methods unless otherwise stated. Besides, terms used herein should be understood as meaning usually used in this technical field unless otherwise stated.

<Transformation Method for Gram-Positive Bacteria>

The transformation method for gram-positive bacteria of the present invention comprises using a helper plasmid having an inactivated origin of DNA transfer (oriT) region in conjugational transfer.

In the present invention, gram-positive bacteria refer to bacteria and other fungi positive in gram staining. The gram-positive bacteria generally have a comparatively thick (15 nm to 80 nm) cell walls, and many of these do not contain lipopolysaccharide in cell coat. Besides, many of these are highly sensitive to lysozyme. Specific examples of the gram-positive bacteria include *Bacillus* (such as *Bacillus subtilis*, *Bacillus anthracis*, thermophilic bacteria (*Geobacillus*), *Bacillus cereus*, *Bacillus licheniformis*, *Bacillus megaterium*, *Bacillus pumilus*, and *Bacillus thuringiensis*), *Listeria*, *Staphylococcus*, *Streptococcus*, *Enterococcus* (such as lactic acid bacteria), and *Clostridium*. In the present invention, the gram-positive bacteria are preferably *Bacillus*, among which *Bacillus subtilis*, *Bacillus anthracis* and thermophilic bacteria belonging to the genus *Bacillus* are more preferred, and *Geobacillus kaustophilus* is further preferred.

The term "transformation" herein refers to modification of a genomic DNA of the gram-positive bacteria or modification caused by introducing a DNA into the gram-positive bacteria, and embraces deletion, replication and mutation of a chromosomal DNA and all trait changes caused by introducing an autonomous replicating plasmid. An introduced DNA may be integrated into a chromosome to be retained or replicated, or may be retained or replicated independently of the chromosome like a plasmid or the like. When a DNA is integrated into a specific site of the chromosome of the gram-positive bacteria, homologous recombination technique may be employed.

In the present invention, conjugational transfer is a phenomenon occurring when bacteria having different traits are mixedly cultured, and refers to transfer of a part of a gene of a bacteria (donor bacteria) to other bacteria (recipient bacteria). Intensity of conjugational transfer ability is affected by a gene involved in the conjugational transfer on a chromosome of the donor or on a plasmid contained in the donor. Examples of the gene involved in the conjugational transfer include a self-transmissible gene, a conjugate-transmissible gene and an oriT sequence. A protein encoded by a self-transmissible gene is involved in interaction between donor bacteria and recipient bacteria. A protein encoded by a conjugate-transmissible gene has a function to nick an oriT sequence and a function to stably carry a DNA having been single stranded. The oriT sequence contains a nick site and a recognition sequence for nicking. The conjugational transfer occurs only when these three exist together.

The term "helper plasmid" herein refers to a plasmid that helps, in transferring a given gene to target bacteria, the transfer of the gene to the bacteria, and a specific example includes pLS20 used for *Bacillus subtilis*. When bacteria containing a helper plasmid are used in transformation, transformation efficiency, simplicity of procedures and necessary time efficiency can be largely improved as compared with those in natural transformation.

The term "origin of DNA transfer (oriT) region" herein refers to a region including a start sequence for the transfer of a DNA.

Now, the transformation method for gram-positive bacteria of the present invention will be specifically described. Specifically, the transformation method for gram-positive bacteria of the present invention includes the steps of:

(1) preparing donor bacteria containing a helper plasmid having an inactivated origin of DNA transfer (oriT) region, and a chromosomal DNA or plasmid having the origin of DNA transfer (oriT) region integrated therein; and (2) performing conjugational transfer from the donor bacteria to recipient bacteria.

The transformation method for gram-positive bacteria of the present invention preferably further includes, if necessary, the step (3) of accumulating a desired DNA segment in a chromosome in the recipient bacteria.

[Step (1)]

(Step of Constructing Recipient Strain (Recipient Bacteria))

As the recipient strain (recipient bacteria), *Bacillus* can be preferably used, and *Bacillus subtilis, Bacillus anthracis* and thermophilic bacteria can be more preferably used, and *Bacillus subtilis* can be further preferably used as described above. In order that it can be checked in the step (2) whether or not transformation has been caused by the conjugational transfer, an antibiotic resistant gene is introduced into such a recipient strain (recipient bacteria) in advance. The antibiotic resistant gene can be introduced into the recipient strain (recipient bacteria) by a method conventionally known to those skilled in the art.

For example, when *Bacillus subtilis* is used as the recipient strain (recipient bacteria), a gene such as comK of *Bacillus subtilis* can be introduced by inactivation through substitution with a spectinomycin resistant gene or the like. Specifically, two DNA fragments respectively corresponding to upstream and downstream regions of the gene such as comK are amplified by PCR using a *Bacillus subtilis* DNA as a template. At this point, primers suitable for an upstream fragment and a downstream fragment are designed and used. Besides, another DNA fragment containing a spectinomycin resistant gene of another *Bacillus subtilis* strain such as TMO310 is amplified by using a proper primer. These three fragments are linked by recombinant PCR to insert the spectinomycin resistant gene between the upstream region and the downstream region of the gene such as comK. When *Bacillus subtilis* is transformed to introduce the recombinant PCR fragment into the recipient strain, the resistance against an antibiotic such as spectinomycin can be imparted, and thus, a novel *Bacillus subtilis* strain resulting from modification of the recipient strain can be obtained in the present invention.

(Step of Constructing Helper Plasmid containing Inactivated oriT Region)

The inactivation of an oriT region of a helper plasmid can be performed in accordance with a genetic manipulation method conventionally known to those skilled in the art. It is noted that the inactivation of the oriT region embraces partial deletion of the oriT region, whole deletion of the oriT region, and substitution of one or more bases of the oriT region. For example, the oriT region can be inactivated through deletion by a method such as marker-free deletion. Now, a case where pLS20cat is used as the helper plasmid will be described.

Two DNA fragments respectively corresponding to the upstream region (fragment 1) and the downstream region (fragment 2) of $oriT_{LS20}$ of pLS20cat are amplified by PCR with a pLS20cat DNA used as a template and by using primers oriT-uF/oriT-uR and oriT-dF/ori for the upstream region. Since an end portion of the fragment 1 and a head portion of the fragment 2 are the same in 22 bp, such portions can be used for deleting the oriTLszo region by the transformation. Another DNA fragment (fragment 3) of a mazF kan cassette is amplified from a TMO311 DNA by using mazF-F/mazF-R as a primer. The three PCR fragments can be designed, by recombinant PCR using oriT-uF/oriT-dR as a primer, so as to be linked in the order of the fragment 1, the fragment 3 and the fragment 2. Next, the thus obtained recombinant PCR fragment is transformed into PKS11 to impart kanamycin resistance, and thus, a novel strain YNB022 can be obtained. In this strain, pLS20cat is modified by integrating the PCR fragment via a double crossing-over event of the oriTLszo region. YNB022 is grown in an LB liquid medium containing kanamycin at 37° C. about overnight. An aliquot of the culture fluid is transferred to a fresh LB liquid medium containing 1 mM isopropyl thio-galactopyranoside (IPTG) to grow cells at 37° C. for about 2 hours. Next, an aliquot of the culture fluid is spread on an LB plate containing 1 mM IPTG and incubated at 37° C. about overnight. In the presence of IPTG mazF is expressed to produce a suicide toxin, and hence, merely cells capable of coming out of the mazF kan cassette can survive by intermolecular recombination. A kanamycin-sensitive colony, out of colonies appearing on the plate, can be subjected to sequencing to confirm that the $oriT_{LS20}$ region has been properly deleted. The primers are shown in Table 2 below.

(Step of Constructing Donor Strain)

As a donor strain (donor bacteria), *Bacillus* can be preferably used, and *Bacillus subtilis, Bacillus anthracis* and thermophilic bacteria can be more preferably used, and *Bacillus subtilis* can be further preferably used as described above. In this step, the *Bacillus subtilis*, prepared as described above, into which the helper plasmid containing the inactivated oriT region has been introduced in advance is used for producing the donor strain, and the oriT region derived from the helper plasmid is integrated into the chromosomal DNA. Alternatively, a plasmid can be transferred instead of the chromosomal DNA, but in this case, a plasmid containing the oriT region derived from the helper plasmid is introduced into the *Bacillus subtilis* into which the helper plasmid containing the inactivated oriT region has been introduced in advance, and thus, the donor strain usable in the step (2) is prepared.

A method for integrating the oriT region derived from the helper plasmid into the chromosomal DNA of the donor strain can be performed in accordance with a genetic manipulation method conventionally known to those skilled in the art. Now, this step will be described by assuming, for example, a case where *Bacillus subtilis* YNB060 is to be constructed as the donor strain by using pLS20cat as the helper plasmid.

Specifically, primers yhfM-uF/yhfM-uR1 (for the upstream region) and yhfM-dF/yhfM-dR (for the downstream region) are used to amplify, from the DNA of *Bacillus subtilis* 168, two fragments respectively corresponding to the upstream region (fragment 1) and the downstream region (fragment 4) of yhfM. A fragment 2 containing $oriT_{LS20}$ is amplified by using a primer oriT-F/oriT-R with pLS20cat used as a template. Besides, a fragment 3 having an erythromycin resistant gene is amplified by using a primer erm-F 1/erm-R with a plasmid pMutin2 used as a template. The fragments 1 to 4 are linked through the recombinant PCR using a primer yhfM-uF/yhfM-dR in the order of the fragment 1, the fragment 2, the fragment 3 and the fragment 4. TMO311 (aprE:kan) is transformed with the resultant recombinant PCR fragment, and a colony resistant to both erythromycin and kanamycin can be selected to be defined as the donor strain (YNB060).

[Step (2)]

In this step, the conjugational transfer from the donor strain described above to a recipient strain is performed. The donor strain and the recipient strain are respectively cultured in LB liquid media respectively containing proper antibiotics under shaking at 180 rpm at 37° C. about overnight. Each of the thus obtained cultures is diluted, in a fresh LB medium not containing an antibiotic, to a cell density of OD600 of about 0.05, and the resultant is incubated under shaking at 180 rpm at 37° C. When OD600 reaches 0.5 to 0.7, 500 µL of the donor culture and 500 µL of the recipient culture are mixed in a 1.5 mL microtube, and the resultant mixture is allowed to stand still at 37° C. for 2 minutes to 2 hours, preferably 5 minutes to 1 hour, more preferably 10 minutes to 30 minutes, and further preferably about 15 minutes. A step of the conjugational transfer conventionally takes several hours or more, but adequate transfer can be attained even in about 15 minutes by the method of the present invention. The mixture is continuously diluted, and spread over LB plates respectively containing various combinations of antibiotics, so as to grow colonies overnight. In each of these plates, a colony forming unit (CFU) is measured for calculating transformation efficiency through the conjugational transfer, and thus, CFU×$10^6$ (ppm) of transformed CFU/total recipient is obtained.

[Step (3)]

In this step, a desired DNA segment is accumulated in the chromosome of the recipient bacteria. Specifically, the desired DNA segment can be accumulated in the chromosome of the recipient cells by repeatedly performing the steps (1) and (2) using transformed cells obtained by the conjugational transfer of the step (2), as recipient bacteria.

In the transformation method of the present invention, when the donor strain and the recipient strain are different species, a DNA to be conjugationally transferred may be degraded by a restriction enzyme or the like in the recipient strain in some cases. In such a case, in the step (1), transformation for introducing a methyltransferase into the donor strain may be performed in advance so that DNA modification (methylation modification or the like) similar to that in the recipient strain can be performed in the donor strain. For example, when thermophilic bacteria (*Geobacillus kaustophilus*; GK) are used as the recipient strain, a method disclosed in JP 2011-211968 A can be employed. Specifically, efficiency can be further improved by performing, on a donor for plasmid transfer to GK, genetic manipulation for imparting DNA methylase and for forced enhancement of rap gene expression. Besides, as a plasmid (pGK1) to be transferred to GK, for example, a plasmid obtained by adding, to pGR16B, ori for replication in GK and a kanamycin resistant gene KmR (TK101) or the like capable of enduring a high temperature necessary for selection in GK can be used.

EXAMPLES

The present invention will be specifically described with reference to the following examples, and it is noted that the present invention is not limited to these examples.

Example 1

Transformation Method for *Bacillus subtilis*

1. Bacterial Strain and Culture Conditions

Bacterial strains and plasmids used in this study are shown in Table 1 below. Besides, synthetic oligonucleotides used as PCR primers are shown in Table 2 below (SEQ ID NOS: 1 to 33). The bacterial strain was grown in an LB medium (manufactured by Difco) under a condition of 37° C. to be used. If necessary, an antibiotic (5 µg/mL chloramphenicol, 1 µg/mL erythromycin, 100 µg/mL spectinomycin, and 10 µg/mL kanamycin) was added to the medium.

TABLE 1

| Strains and plasmids | | Relevant genotype or description |
|---|---|---|
| Strains (*B. subtilis*) | PKS11 | trpC2 pLS20cat |
| | GR138 | trpC2 pLS20cat pGR16B |
| | TMO310 | trpC2 aprE::(spc lacI Pspac-mazF) |
| | TMO311 | trpC2 aprE::(kan lacI Pspac-mazF) |
| | YNB001 | trpC2 comK::spc |
| | YNB022 | trpC2 pLS20cat (kan lacI Pspac-mazF) |
| | YNB026 | trpC2 pLS20catΔoriT |
| | YNB031 | trpC2 pLS20catΔoriT pGR16B |
| | YNB060 | trpc2 aprE::kan yhfM::(oriTLS20-F erm) |
| | YNB061 | trpc2 aprE::kan yhfM::(oriTLS20-R erm) |
| | YNB069 | trpc2 aprE::kan yhfK::(oriTLS20-F erm) |
| | YNB062 | trpc2 aprE::kan yhfC::(oriTLS20-F erm) |
| | YNB097 | trpc2 aprE::kan yhcT::(oriTLS20-F erm) |
| | YNB065 | trpc2 aprE::kan yhfM::(oriTLS20-F erm) pLS20cat |
| | YNB066 | trpc2 aprE::kan yhfM::(oriTLS20-R erm) pLS20cat |
| | YNB071 | trpc2 aprE::kan yhfK::(oriTLS20-F erm) pLS20cat |
| | YNB067 | trpc2 aprE::kan yhfC::(oriTLS20-F erm) pLS20cat |

TABLE 1-continued

| Strains and plasmids | | Relevant genotype or description |
|---|---|---|
| | YNB099 | trpc2 aprE::kan yhcT::(oriTLS20-F erm) pLS20cat |
| | YNB091 | trpc2 aprE::kan yhfM::(oriTLS20-F erm) pLS20catΔoriT |
| | YNB095 | trpc2 aprE::kan yhfM::(oriTLS20-R erm) pLS20catΔoriT |
| | YNB092 | trpc2 aprE::kan yhfK::(oriTLS20-F erm) pLS20catΔoriT |
| | YNB094 | trpc2 aprE::kan yhfC::(oriTLS20-F erm) pLS20catΔoriT |
| | YNB100 | trpc2 aprE::kan yhcT::(oriTLS20-F erm) pLS20catΔoriT |
| Plasmids | pLS20cat | Conjugative plasmid pLS20 with a chloramphenicol resistant gene inserted in the unique Sal1 site |
| | pLS20catΔoriT | pLS20cat without oriT LS20 |
| | pGR16B | mobile plasmid containing oriT LS20 |

TABLE 2

| Oligonucleotides used in this study | Sequences (5'→3') |
|---|---|
| spc-F | GAGTCAGAAAACAGACGCATAAACGCTAACGGTCAGC |
| spc-R | CTAATACCGTTCCCCGAGAAGCTTCACTAAATTAAAGTAATAAAGC |
| comK-uF | AGAGCGTAAGAAACGCATC |
| comK-uR | TGCGTCTGTTTTCTGACTC |
| comK-dF | CTCGGGGAACGGTATTAG |
| comK-dR | CGAAGATCTGCCTACTGAAC |
| oriT-uF | TAAATAACATGACTGTGGAAATGAC |
| oriT-uR | GCTTGAGTCAATTCCGCTGTCGTTAGTCTTCGATGACGAGATTG |
| oriT-dF | CTGATTGGGTAGGATCCCCGAGAAAGAGCAATCTCGTCATCGAAGACTAAAAAAGAAACACTTATTTGAACAGATC |
| oriT-dR | GCGTCTTCTTAAAACGCTG |
| mazF-F | CGACAGCGGAATTGACTCAAGC |
| mazF-R | CGGGGATCCTACCCAATCAG |
| oriT-F | AAAGAGCAATCTCGTCATCGAAGACTAAATTTC |
| oriT-R | TTGTTAACGCTCCTTTTCATCGATTTCTG |
| erm-F1 | CAGAAATCGATGAAAAGGAGCGTTAACAAGAGTGTGTTGATAGTGCAGTATC |
| erm-F2 | GAAATTTAGTCTTCGATGACGAGATTGCTCTTTGAGTGTGTTGATAGTGCAGTATC |
| erm-R | CTACATTCCCTTTAGTAACGTGTAAC |
| yhM-uF | GATCGTGAAAGGCCCCAATGTG |
| yhfM-uR1 | CAGAAATCGATGAAAAGGAGCGTTAACAAGAAGCAAAGGATTGAAAATGAAAAGCG |
| yhfM-dF | GTTACACGTTACTAAAGGGAATGTAGCACTATTTTTTTCATTTGCATCACTCCAAAC |
| yhfM-dR | ATCAGCGAAAGCACAAACACAAAACC |
| yhfK-uF | ATGATAAAATGACCACCGAAGAATTCCG |
| yhfK-uR1 | GAAATTTAGTCTTCGATGACGAGATTGCTCTTTCACTTTCATGTGAATCCCTCCTGCC |
| yhfK-dF | GTTACACGTTACTAAAGGGAATGTAGGAAACTATGACAGTACTGACACTCAGGGC |
| yhfK-dR | GACGAGCTCAACCTTTGGCAGC |
| yhfC-uF | GCCAAATGGAGGCCGTATGTCAG |
| yhfC-uR1 | GAAATTTAGTCTTCGATGACGAGATTGCTCTTTTGACCATTTTTCAGCCTCCTTTTTCTTTTTC |
| yhfC-dF | GTTACACGTTACTAAAGGGAATGTAGGATTGTAAAAGCAAAAAGGGTGTTTCAATAAAAGG |
| yhfC-dR | GGCTTGGGATCGATACAAGTTCTTTAATGAG |
| yhcT-uF | TTCGGGGACGAAAAATAGCACAGATC |
| yhcT-uR1 | GAAATTTAGTCTTCGATGACGAGATTGCTCTTTCTGCTGATATGAAAAACCTTTGCCG |
| yhcT-dF | GTTACACGTTACTAAAGGGAATGTAGAGCCCTCTGCCTTTTTGGTTCATG |
| yhcT-dR | GCTTTGTTAGTCTTCTTTTGAAAGTCAGAAAAAGC |

2. Construction of Recipient Strain

The comK gene of *Bacillus subtilis* 168 was inactivated by substitution with a spectinomycin resistant gene. Specifically, two DNA fragments respectively corresponding to the upstream and downstream regions of comK were amplified by PCR using the DNA of *Bacillus subtilis* 168 as a template. As primers, comK-uF/comK-uR was used for the upstream fragment, and comK-dF/comK-dR was used for the downstream fragment. Besides, another DNA fragment containing a spectinomycin resistant gene of TMO310 was amplified by using a primer spc-F/spc-R. These three fragments were linked by the recombinant PCR using comK-uF/comK-dR, so as to insert the spectinomycin resistant gene between the upstream and downstream regions of comK. The resultant recombinant PCR fragment was introduced to transform *Bacillus subtilis* 168 to be spectinomycin resistant, and thus, a novel *Bacillus subtilis* strain YNB001 (comK:spc) to be used as a recipient strain in this study was obtained.

3. Construction of pLS20catΔoriT

The oriT$_{LS20}$ region of pLS20cat was inactivated by marker-free deletion.

Specifically, two DNA fragments respectively corresponding to the upstream region (fragment 1) and the downstream region (fragment 2) of oriT$_{LS20}$ were amplified by PCR by using the primers oriT-uF/oriT-uR and oriT-dF/ori for the upstream region with the DNA of pLS20cat used as a template. Since an end portion of the fragment 1 and a head portion of the fragment 2 were the same in 30 bp, these portions were used for deleting the oriT$_{LS20}$ region by the transformation. Another DNA fragment (fragment 3) of a mazF kan cassette was amplified from a TMO311 DNA by using masF-F/mazF-R as a primer. These three PCR fragments were designed to be linked by the recombinant PCR using oriT-uF/oriT-dR as a primer in the order of the fragment 1, the fragment 3 and the fragment 2. The thus obtained recombinant PCR fragment was introduced to transform PKS11 to be resistant to kanamycin, and thus, a novel strain YNB022 was obtained. In this strain, pLS20cat was modified by integrating the PCR fragment via a double crossing-over event of the oriT$_{LS20}$ region. YNB022 was grown in an LB liquid medium containing kanamycin at 37° C. overnight. An aliquot of the culture fluid was transferred to a fresh LB liquid medium containing 1 mM isopropyl thiogalactopyranoside (IPTG) to grow cells at 37° C. for 2 hours. Next, an aliquot of the culture fluid was spread on an LB plate containing 1 mM IPTG, and incubated at 37° C. overnight. In the presence of IPTG mazF was expressed to produce a suicide toxin, and hence, merely cells capable of coming out of the mazF kan cassette could survive by intermolecular recombination. A kanamycin-sensitive colony, out of colonies appearing on the plate, was subjected to sequencing to confirm that the oriT$_{LS20}$ region had been properly deleted. The thus obtained plasmid was named pLS20catΔoriT. The structure of this plasmid is illustrated in FIG. 1. Besides, its gene sequence is shown in sequence listing as SEQ ID NO: 34.

4. Construction of Donor Strain

Figure 2:
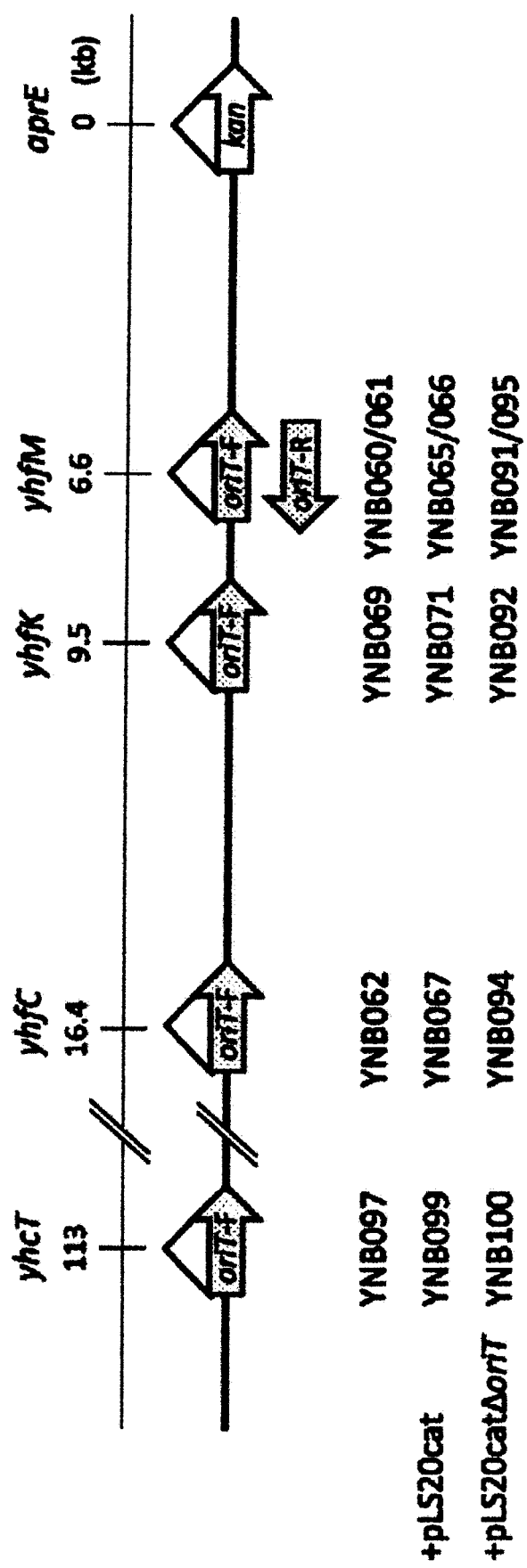
FIG. 2 is a schematic diagram of a locus of oriT$_{LS20}$ and integration of kanamycin resistant gene of a donor strain.

The donor strain YNB060 was constructed as follows (FIG. 2). The primers yhfM-uF/yhfM-uR1 (for the upstream region) and yhfM-dF/yhfM-dR (for the downstream region) were used to amplify, from the 168 DNA, two fragments respectively corresponding to the upstream region (fragment 1) and the downstream region (fragment 4) of yhfM. A fragment 2 containing oriT$_{LS20}$ was amplified by using a primer oriT-F/oriT-R with pLS20cat used as a template. Besides, a fragment 3 having an erythromycin resistant gene was amplified by using a primer erm-F1/erm-R with a plasmid pMutin2 used as a template. The fragments 1 to 4 were linked through the recombinant PCR using a primer yhfM-uF/yhfM-dR in the order of the fragment 1, the fragment 2, the fragment 3 and the fragment 4. The thus obtained recombinant PCR fragment was introduced to transform TMO311 (aprE:kan) to be resistant to both erythromycin and kanamycin, and a colony was selected. The thus obtained strain was named YNB060. This strain has an erythromycin marker at oriT$_{LS20}$, and has a kanamycin marker at both yhfM and aprE loci present on the same chromosome but away from each other by 6.6 kb. Besides, a replication direction of oriT$_{LS20}$ is a direction toward the kanamycin marker present downstream by 6.6 kb.

Another strain YNB061 was constructed in the same manner as described above. Two fragments of yhfM (of upstream and downstream regions) were amplified by using primers yhfM-uF/yhfM-uR2 and yhfM-dF/yhfM-dR, respectively. Primers oriT-F/oriT-R and erm-F2/erm-R were used to amplify an oriT$_{LS20}$ fragment (fragment 2) and an erythromycin resistant fragment (fragment 3), respectively. The thus obtained four fragments were linked by the recombinant PCR using primer yhfM-uF/yhfM-dR. The thus obtained recombinant PCR fragment was introduced to transform TMN311 to be resistant to erythromycin, and a colony was selected to obtain YNB061. In contrast to YNB060, the replication direction of oriT$_{LS20}$ at the yhfM locus was opposite to the kanamycin marker present at the aprE locus in YNB061.

As still other strains, YNB069, YNB062 and YNB097 were constructed in the same manner as described above (FIG. 2). As for YNB069, yhfK-uF/yhfK-uR1 and yhfK-dF/yhfK-dR (Table 2) were used as primers, respectively to amplify, from the 168 DNA, two fragments of the upstream region (fragment 1) and the downstream region (fragment 4) of yhfK. As for YNB062, yhfC-uF/yhfC-uR1 and yhfC-dF/yhfC-dR were used as primers, respectively to amplify two fragments of the upstream region and the downstream region of yhfC. As for YNB097, yhcT-uF/yhcT-uR1 and yhcT-dF/yhcT-dR were used as primers, respectively to amplify two fragments of the upstream region and the downstream region of yhcT. The oriT$_{LS20}$ fragment (fragment 2) and the erythromycin resistant fragment (fragment 3) were the same as those used in the construction of YNB060 described above. As for each of these strains, the four fragments were linked by the recombinant PCR using a primer yhfK-uF/yhfK-dR for YNB069, a primer yhfC-uF/yhfC-dR for YNB062, and a primer yhcT-uF/yhcT-dR for YNB097. Each of the thus obtained recombinant PCR fragments was used to transform TMO311 (aprE:kan), and a colony resistant to both erythromycin and kanamycin was selected. The thus obtained strains were named YNB069, YNB062 and YNB097. All of these strains have the erythromycin marker as well as oriT$_{LS20}$ at yhfK, yhfC and yhcT loci. These are positioned, on the chromosome, away from the kanamycin marker at the aprE locus by respectively 9.5 kb, 16.4 kb and 113 kb. Besides, in all of these strains, the replication direction of oriT$_{LS20}$ was the forward direction toward the kanamycin marker.

From each of the strains YNB060, YNB061, YNB069, YNB062 and YNB097 obtained as described above, a chromosomal DNA was extracted by an ordinary method, and was introduced into the strain 168 (PKS11) containing pLS20cat or YNB026 containing pLS20catΔoriT to obtain a donor strain to be used in experiments described below. As strains containing pLS20cat, strains YNB065, YNB066, YNB071, YNB067 and YNB099 were obtained, and as strains containing pLS20catΔoriT, strains YNB091, YNB095, YNB092, YNB094 and YNB100 were obtained.

5. Conjugational Transfer of DNA

The conjugational transfer of a DNA was performed in a liquid medium. Specifically, the donor strain and the recipient strain were respectively cultured in 5 mL of LB liquid media containing proper antibiotics under shaking at 180 rpm at 37° C. overnight. Each of the thus obtained cultures was diluted, in 5 mL of a fresh LB medium not containing an antibiotic, to a cell density of OD600 of 0.05, and the resultant was incubated under shaking at 180 rpm at 37° C. When OD600 reached 0.5 to 0.7, 500 µL of the donor culture and 500 µL of the recipient culture were mixed in a 1.5 mL microtube, and the resultant mixture was allowed to stand still at 37° C. for 15 minutes. The mixture was serially diluted, and spread over LB plates respectively containing various combinations of antibiotics, so as to grow colonies overnight. In each of these plates, a colony forming unit (CFU) was measured for calculating transformation efficiency through the conjugational transfer (transconjugate), and thus, CFU×10$^6$ (ppm) of transformed CFU/total recipient was obtained.

6. Result

As a result of the above-described experiment, it was found that pLS20catΔoriT (plasmid having oriT deleted) itself cannot transfer to the recipient strain but retains the ability to transfer, to a recipient strain, a plasmid containing oriT$_{LS20}$ or a chromosomal DNA existing together. This will be described in detail.

(Experiment of Plasmid Transfer)

Figure 3:
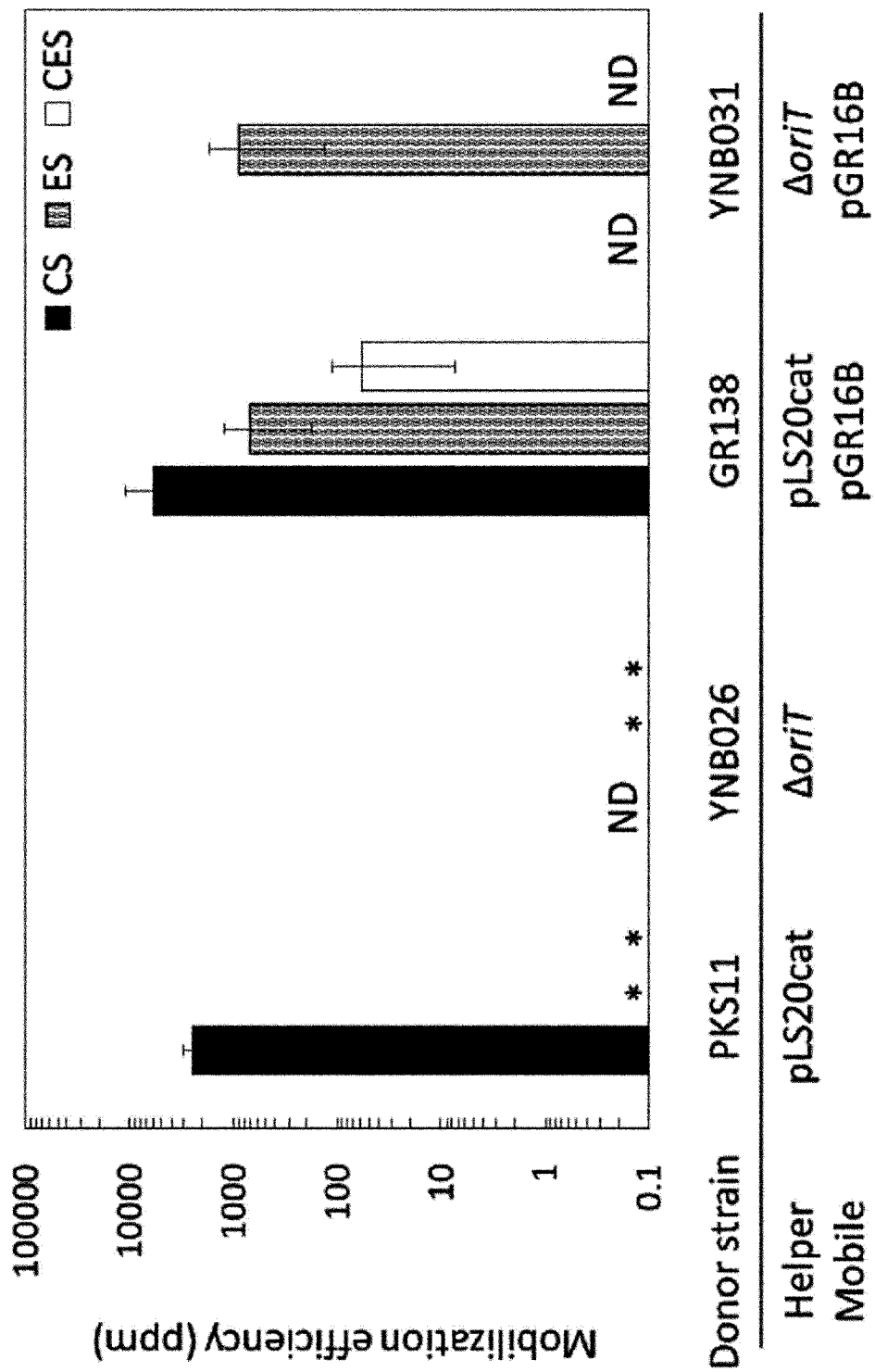
FIG. 3 is a diagram illustrating mobilization efficiencies of transfer plasmid pGR16B, and helper plasmids pLS20cat and pL20catΔoriT.

Results of an experiment of plasmid transfer are illustrated in FIG. 3. In FIG. 3, CS (black column) corresponds to a concentration (ppm) of cells having acquired chloramphenicol resistance, ES (gray column) corresponds to a concentration (ppm) of cells having acquired erythromycin resistance, and CES (white column) corresponds to a concentration (ppm) of cells having acquired chloramphenicol resistance and erythromycin resistance. Besides, ND indicates that a concentration was below detection limit (<0.01 ppm), and * indicates that a corresponding experiment was not performed.

As illustrated in FIG. 3, pLS20cat was transferred from the donor strain PKS11 (the strain 168 containing pLS20cat) or GR138 (the strain 168 containing pLS20cat and pGR16B) to the recipient strain, resulting in obtaining a large number of recipient cells (2,500 ppm or more) having acquired chloramphenicol resistance. Besides, the donor strain GR138 containing the helper plasmid pLS20cat and transfer plasmid pGR16B (containing oriTLszo and erythromycin resistant gene) imparted the erythromycin resistance to the recipient strain, and hence, it was found that pLS20cat can mediate the transfer of the transfer plasmid pGR16B containing $oriT_{LS20}$ (FIG. 3). In the above-described experiment, since the donor strain GR138 imparted the erythromycin resistance to about 1,000 ppm of the recipient cells, it can be said that the helper plasmid pLS20cat has approximately double efficiency in the transformation of recipient cells as compared with the transfer plasmid pGR16B. Besides, since about 100 ppm of the recipient cells exhibited resistance to both erythromycin and chloramphenicol (FIG. 3), it is suggested that there is a possibility that about 10% of trans-zygotes having received pGR16B have acquired pLS20cat.

It is known that since bacteria having pLS20cat do not accept pLS20cat-mediated gene transfer, a transformant having received pLS20cat cannot be transformed again by using the same conjugational transfer system. On the other hand, as revealed by the above-described experiment, cells having pLS20cat could further transfer, to another strain, not only pLS20cat itself but also pGR16B. If such trans-zygotes are released to the environment, there might be a possibility that the antibiotic resistant gene is spread to other bacterial cells to cause novel antibiotic resistant bacteria to appear.

Therefore, in order to avoid autotransfer of pLS20cat, the present inventors constructed pLS20catAoriT by knocking out $oriT_{LS20}$ of pLS20cat by the above-described method. As expected, YNB026, that is, the donor strain containing pLS20catAoriT, did not transfer pLS20catAoriT at all, but YNB031 containing pLS20catAoriT and pGR16B could transfer pGR16B alone to impart erythromycin resistance to the recipient strain (FIG. 3). Besides, the mobilization efficiency of pGR16B was substantially the same when pLS20cat was used as the helper plasmid and when pLS20catΔoriT was used as the helper plasmid. These results reveal that the pLS20cat-dependent transfer of pGR16B does not require self-mobility of pLS20cat of the helper plasmid. Furthermore, the knockout of oriT in pLS20cat did not affect the mobilization efficiency of pGR16B existing together.

(Experiment of Chromosomal DNA Transfer)

Figure 4:
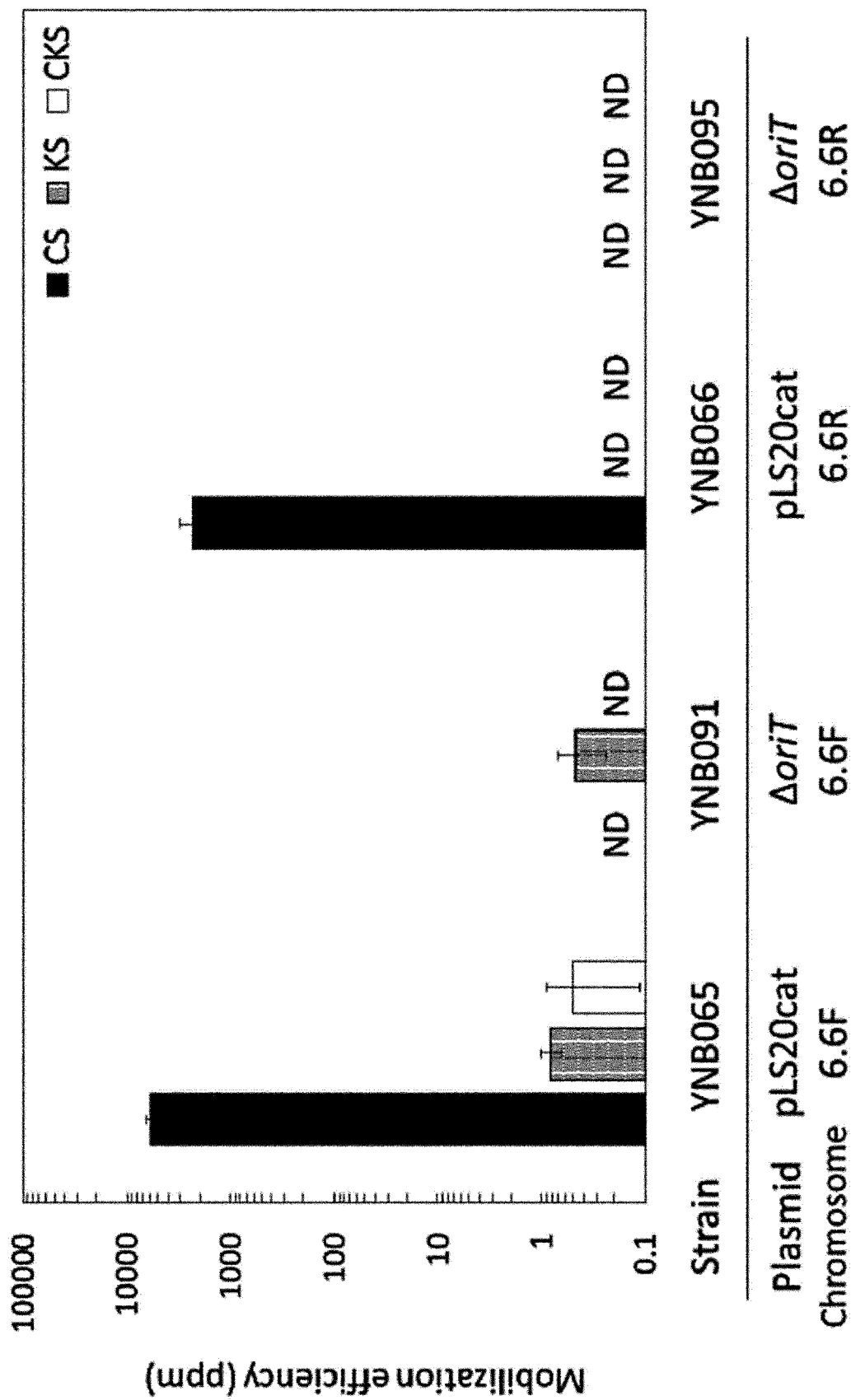
FIG. 4 is a diagram illustrating mobilization efficiencies of a chromosomal DNA, and the helper plasmids pLS20cat and pLS20catΔoriT.

Next, the present inventors checked whether or not pLS20catAoriT could mediate the transfer of a chromosomal DNA depending on the state of the $oriT_{LS20}$ region. Results are illustrated in FIG. 4. In FIG. 4, CS (black column) corresponds to a concentration (ppm) of cells having acquired chloramphenicol resistance, KS (gray column) corresponds to a concentration (ppm) of cells having acquired kanamycin resistance, and CKS (white column) corresponds to a concentration (ppm) of cells having acquired chloramphenicol resistance and kanamycin resistance. Besides, ND indicates that a concentration was below detection limit (<0.01 ppm).

In a donor chromosome of each of YNB060 and YNB061, $oriT_{LS20}$ was introduced into the yhfM locus present upstream by 6.6 kb from a kanamycin resistant gene at the aprE locus. A replication direction of $oriT_{LS20}$ was the forward direction to and the reverse direction from the kanamycin resistant gene respectively in the strains YNB060 and YNB061. pLS20cat or pLS20catAoriT was introduced into the donor as the helper plasmid to produce new strains (1) YNB065 (pLS20cat introduced into YNB060), (2) YNB066 (pLS20cat introduced into YNB061), (3) YNB091 (pLS20catAoriT introduced into YNB060), and (4) YNB095 (pLS20catAoriT introduced into YNB061). On the other hand, in a recipient strain YNB001, comK encoding a transcription factor indispensable to natural competence was inactivated to completely eliminate natural competence (which data is not shown).

pLS20cat of both YNB065 and YNB066 imparted the chloramphenicol resistance to 2,300 ppm or more of recipient cells. On the other hand, with respect to impartation of the kanamycin resistance, YNB065 imparted the kanamycin resistance to merely 1 ppm of recipient cells but YNB066 did not impart the kanamycin resistance at all (FIG. 4). These results reveal that when the replication direction of $oriT_{LS20}$ is the forward direction to the kanamycin resistant gene, pLS20cat can transfer the kanamycin resistant gene present downstream by 6.6 kb from $oriT_{LS20}$. Here, since the recipient did not have natural competence, it can be said that the acquisition of the kanamycin resistance depended on the conjugational transfer alone. On the other hand, YNB065 imparted, to the recipient cells (about 1 ppm of the recipient cells), not only the kanamycin resistance but also the chloramphenicol resistance (FIG. 4). This result suggests that most of recipient cells having acquired the kanamycin resistance through the introduction of the large chromosomal DNA can further acquire the helper plasmid pLS20cat.

In the experiment using YNB091 and YNB095 obtained by introducing pLS20catAoriT as the helper plasmid respectively into YNB060 and YNB061, the recipient cells did not acquire the chloramphenicol resistance, and it was confirmed that pLS20catAoriT had lost automobility (FIG. 4). On the other hand, more significantly, when YNB091 was used as the donor cells, pLS20catAoriT imparted the kanamycin resistance to recipient cells with the same efficiency as pLS20cat dependently on the orientation of oriTLszo. This result reveals that pLS20catAoriT not only can transfect the transfer plasmid but also can exhibit helper activity in transfecting a chromosomal DNA efficiently in the same manner as the original helper plasmid pLS20cat. Since YNB095 did not impart the kanamycin resistance to the recipient, it was confirmed that the DNA transfection depends on $oriT_{LS20}$ in the forward direction.

Figure 5:
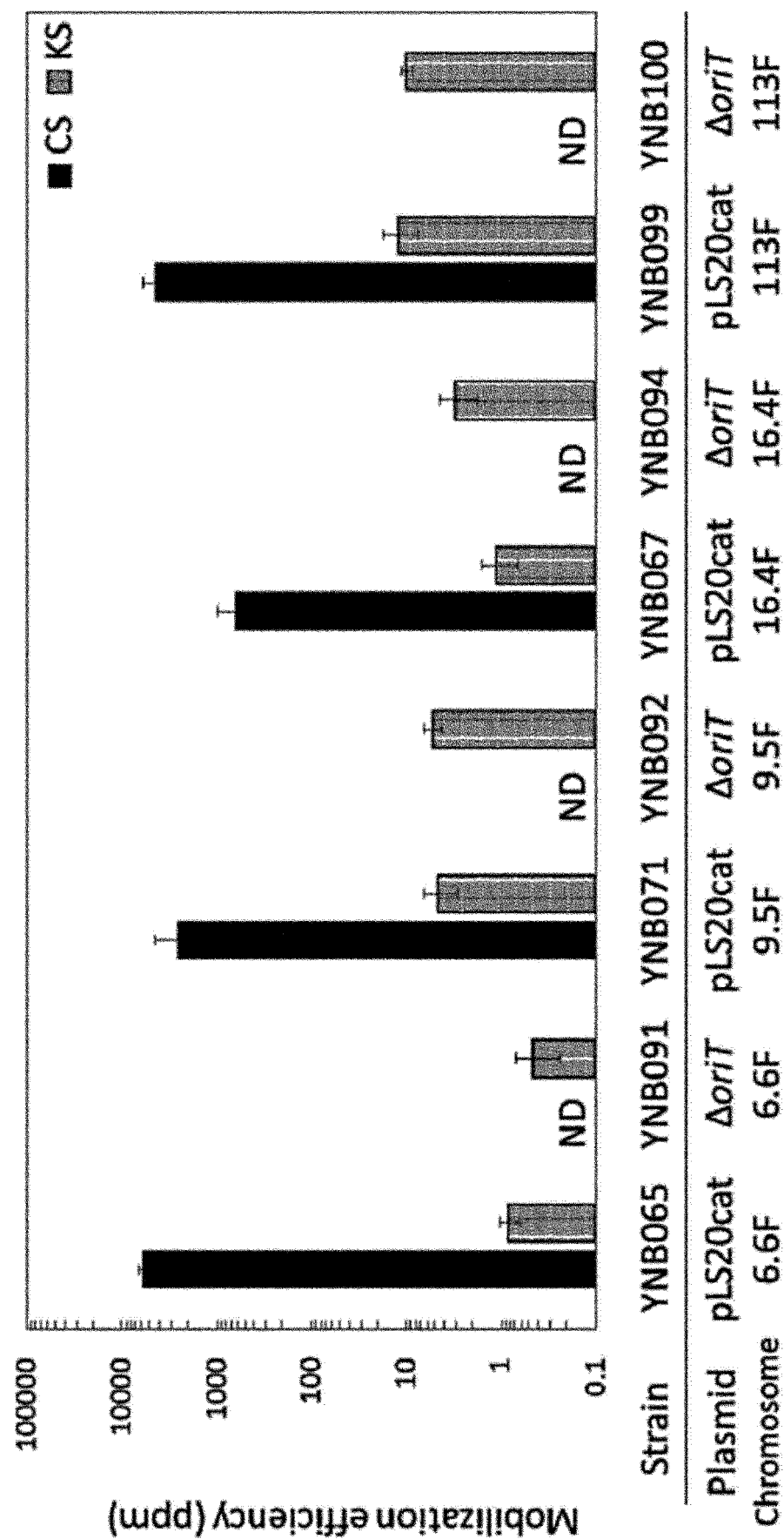
FIG. 5 is a diagram illustrating mobilization efficiencies of a chromosomal DNA, and the helper plasmids pLS20cat and pLS20catΔoriT.

Next, the present inventors performed an experiment for checking the length of a chromosomal DNA that can be mediated to be transferred by pLS20catAoriT. Results are illustrated in FIG. 5. In FIG. 5, CS (black column) corresponds to a concentration (ppm) of cells having acquired chloramphenicol resistance, and KS (gray column) corresponds to a concentration (ppm) of cells having acquired kanamycin resistance. Besides, ND indicates that a concentration was below detection limit (<0.01 ppm).

Distances between oriT$_{LS20}$ and the kanamycin marker in the strains YNB069, YNB062 and YNB097 were 9.5 kb, 16.4 kb, and 113 kb, respectively. In all of these strains, the replication direction of oriT$_{LS20}$ was the forward direction to the kanamycin resistant gene. The strains YNB071 (pLS20cat introduced into YNB069), YNB067 (pLS20cat introduced into YNB062), YNB099 (pLS20cat introduced into YNB097), YNB092 (pLS20catAoriT introduced into YNB069), YNB094 (pLS20catAoriT introduced into YNB062), and YNB100 (pLS20catAoriT introduced into YNB097) are included. Although all the donors containing pLS20cat imparted the chloramphenicol resistance to the recipient cells over 600 ppm, the other donors containing pLS20catAoriT did not impart the chloramphenicol resistance at all (FIG. 5). More significantly, however, all the strains containing pLS20catAoriT could impart the kanamycin resistance to 0.5 to 10.0 ppm of recipient cells (FIG. 5). The efficiency was substantially equivalent to the efficiency achieved by YNB091 working as the donor, and it was revealed that the length of a DNA that can be transfected can be up to at least 113 kb. Besides, pLS20catAoriT exhibited efficiency equivalent to that of pLS20cat in transferring a longer segment of a chromosomal DNA (FIG. 5). These results reveal that the mobility of pLS20cat itself is not required for the helper function to transfer a longer segment of a chromosomal DNA.

Example 2

Transformation Method for GK (*Geobacillus kaustophilus*)

Figure 6:
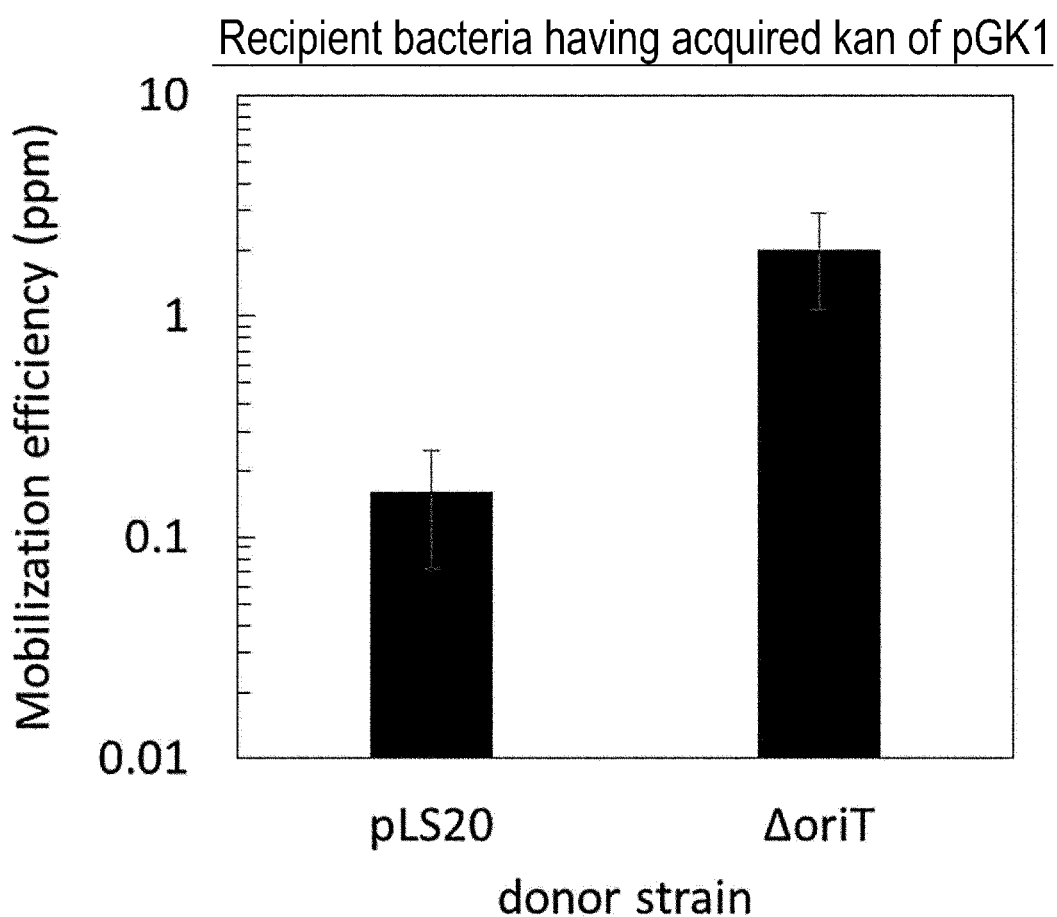
FIG. 6 illustrates comparison between pLS20cat and pLS20catΔoriT in transfer of pGK1 to GK.

An experiment using, as the recipient stain, thermophilic bacteria (*Geobacillus kaustophilus*; GK) was performed. As a method for performing the experiment, a method disclosed in JP 2011-211968 A was employed. Specifically, genetic manipulation for imparting DNA methylase and for forced enhancement of rap gene expression was performed on a donor for plasmid transfer to GK. Besides, as a plasmid pGK1 to be transferred to GK, a plasmid obtained by adding, to pGR16B, ori for replication in GK and a kanamycin resistant gene KmR (TK101) capable of enduring a high temperature necessary for selection in GK was used. At the time of the conjugational transfer, pGK1 mobilization efficiencies attained by using, as the helper plasmid, pLS20cat and pLS20catAoriT were measured. As a result, as illustrated in FIG. 6, it was found that pGK1 can be transferred with higher efficiency when pLS20catAoriT is used than when pLS20cat is used.

INDUSTRIAL APPLICABILITY

According to the transformation method for gram-positive bacteria of the present invention, a large size DNA can be transferred to a recipient side. Besides, since pLS20catAoriT obtained by inactivation of an oriT$_{LS20}$ region in pLS20cat is used as a helper plasmid, the helper plasmid itself is not transferred to the recipient side in conjugational transfer of gram-positive bacteria but transformed cells to which a desired chromosome or plasmid alone has been transferred can be produced. According to the method of the present invention, the obtained transformed cells do not contain the helper plasmid, and hence can be subjected to, as a recipient (recipient bacteria), the conjugational transfer of the desired chromosome or plasmid again in the same manner. Accordingly, a huge DNA can be designed and produced by accumulating a desired DNA segment in a chromosome of a recipient (recipient bacteria) by the present invention. Furthermore, transformation performed by the method of the present invention can be rapidly and simply performed merely by mixing culture fluids of a donor (donor bacteria) and a recipient (recipient bacteria), and hence can be suitably employed for producing microorganisms, cultured cells or the like in synthetic biological industrial activities.

The invention claimed is:

1. A transformation method for gram-positive bacteria by conjugational transfer, comprising:
repeatedly performing conjugational transfer of a DNA segment from a donor bacteria to a recipient bacteria to accumulate DNA segments in a chromosome of the recipient bacteria,
wherein each of the donor bacteria comprises a helper plasmid having an inactivated origin of DNA transfer (oriT) region and a chromosomal DNA or plasmid having the origin of DNA transfer (oriT) region integrated therein.

2. The transformation method according to claim 1, wherein the helper plasmid is a plasmid derived from pLS20cat by inactivation of an origin of DNA transfer (oriT) region therein.

3. The transformation method according to claim 1, wherein the donor bacteria are at least one type of bacteria selected from the group consisting of gram-positive bacteria.

4. The transformation method according to claim 1, wherein the donor bacteria is *Bacillus subtilis*.

5. The transformation method according to claim 1, wherein the recipient bacteria is *Bacillus subtilis*.

6. The transformation method according to claim 1, wherein the recipient bacteria is strain 168.

7. The transformation method according to claim 1, wherein the donor bacteria comprises the chromosomal DNA having the origin of DNA transfer (oriT) region integrated therein.

8. The transformation method according to claim 1, wherein the DNA segments have a size of 100 kb or more.

9. The transformation method according to claim 7, wherein the DNA segments have a size of 100 kb or more.

* * * * *